(12) United States Patent
Guillemont et al.

(10) Patent No.: US 7,638,522 B2
(45) Date of Patent: *Dec. 29, 2009

(54) SALT OF 4-[[4-[[4-(2-CYANOETHENYL)-2,6-DIMETHYLPHENYL]AMINO]-2-PYRIMIDINYL]AMINO] BENZONITRILE

(75) Inventors: Jérôme Emile Georges Guillemont, Ande (FR); Paul Theodoor Agnes Stevens, Turnhout (BE); Alex Herman Copmans, Lille (BE); Jozef Peeters, Beerse (BE); Alfred Elisabeth Stappers, Oud-Turnhout (BE); Roger Petrus Gerebern Vandecruys, Westerlo (BE); Paul Stoffels, Hoogstraten (BE)

(73) Assignee: Janssen Pharmaceutica N.V., Beerse (BE)

( * ) Notice: Subject to any disclaimer, the term of this patent is extended or adjusted under 35 U.S.C. 154(b) by 22 days.

This patent is subject to a terminal disclaimer.

(21) Appl. No.: 11/219,163

(22) Filed: Sep. 2, 2005

(65) Prior Publication Data

US 2006/0111379 A1    May 25, 2006

Related U.S. Application Data

(63) Continuation-in-part of application No. 10/485,636, filed as application No. PCT/EP02/08953 on Aug. 9, 2002, now Pat. No. 7,125,879.

(30) Foreign Application Priority Data

| Aug. 13, 2001 | (EP) | 01203090 |
| Jun. 10, 2002 | (EP) | 02077748 |
| Sep. 3, 2003 | (EP) | 03103275 |
| Sep. 8, 2003 | (EP) | 03103319 |
| Sep. 10, 2003 | (EP) | 03103335 |
| Oct. 2, 2003 | (EP) | 03103668 |
| Sep. 2, 2004 | (MY) | PI20043578 |

(51) Int. Cl.
- *A61K 31/505* (2006.01)
- *C07D 239/48* (2006.01)
- *A61P 31/18* (2006.01)

(52) U.S. Cl. .................... 514/275; 544/323
(58) Field of Classification Search .......... 514/275, 514/323; 544/323

See application file for complete search history.

(56) References Cited

U.S. PATENT DOCUMENTS

| 5,958,935 A | 9/1999 | Davis et al. |
| 6,838,464 B2 | 1/2005 | Pease et al. |
| 7,125,879 B2 * | 10/2006 | Guillemont et al. ......... 514/256 |

FOREIGN PATENT DOCUMENTS

| EP | 0945443 A | 9/1999 |
| EP | 1002795 A | 5/2000 |
| WO | WO 99/50250 | 10/1999 |
| WO | WO 00/27825 A | 5/2000 |
| WO | WO 03/016306 A1 | 2/2003 |
| WO | WO 2004/016581 A1 | 2/2004 |
| WO | WO 2004/050058 A2 | 6/2004 |
| WO | WO 2005/021001 A1 | 3/2005 |

OTHER PUBLICATIONS

International Search Report dated Nov. 26, 2002 for corresponding European Patent Application No. PCT/EP02/08953 (WO2003016306).

International Search Report dated Feb. 7, 2005 for International Application No. PCT/EP2004/052028 (related by subject matter).

Pavia, Andrew T., "Abacavir/Lamivudine in Combination With Efavirenz, Amprenavir/Ritonavir or Stavudine", Internet Article, 'Online!, Jul. 9, 2002, XP002274550.

Young, Benjamin, "Can Abacavir Be Given Once-a-Day?", Internet Article, 'Online!, Sep. 16, 2003, XP002274551.

Gilead Sciences Inc., "Gilead initiates study 934, a 48-week clinical trial evaluating Viread™ and Emtriva™ versus Combivir™", Internet Article, 'Online!, Aug. 11, 2003, XP002314669.

Squires, Kathleen E., "An introduction to nucleoside and nucleotide analogues", Antiviral therapy, vol. 6, suppl. 3, pp. 1-14 (2001) (XP009042950).

D'Auria et al. "Photochemical dimerization in solution of arylacrylonitrile derivatives," Tetrahedron Elsevier Science Publishers, Amsterdam, NL, vol. 53, No. 51, pp. 17307-17316 (Dec. 22, 1997) (p. 17311; Compound No. 7) (XP004106551; ISSN:0040-4020).

* cited by examiner

*Primary Examiner*—Venkataraman Balasubramanian

(57) ABSTRACT

The present invention relates to a pharmaceutical composition comprising as active ingredient the hydrochloric acid salt of 4-[[4-[[4-(2-cyanoethenyl)-2,6-dimethyl-phenyl]amino]-2-pyrimidinyl]amino]benzonitrile and to processes for their preparation.

1 Claim, 8 Drawing Sheets

SALT OF 4-[[4-[[4-(2-CYANOETHENYL)-2,6-DIMETHYLPHENYL]AMINO]-2-PYRIMIDINYL]AMINO] BENZONITRILE

This application, which is a continuation-in-part of U.S. application Ser. No. 10/485,636, filed Feb. 3, 2004 now U.S. Pat. No. 7,125,879, which is a 35 U.S.C. national phase application of PCT/EP02/08953, filed Aug. 9, 2002, which claims priority to EP01203090.4, filed Aug. 13, 2001, and EP02077748.8, filed Jun. 10, 2002, also claims priority to EP05101467.8, filed Feb. 25, 2005; PCT/EP2004/052028, filed Sep. 3, 2004, which although claims priority to (1) EP03103275.8, filed Sep. 3, 2003, (2) U.S. application Ser. No. 60/499,771, filed Sep. 3, 2003, (3) EP03103319.4, filed Sep. 8, 2003, (4) EP03103335.0, filed Sep. 10, 2003, (5) EP03103668.4, filed Oct. 2, 2003, and (6) U.S. application Ser. No. 60/508,486, filed Oct. 3, 2003, priority for applications (1)-(6) herein is not being claimed; and Malaysian application Ser. No. PI20043578, filed Sep. 2, 2004.

WO 03/16306 discloses HIV replication inhibiting pyrimidine derivatives among which 4-[[4-[[4-(2-cyanoethenyl)-2,6-dimethylphenyl]amino]-2-pyrimidinyl]amino]-benzonitrile and the pharmaceutically acceptable salts thereof. WO 04/0162581 discloses processes to prepare 4-[[4-[[4-(2-cyanoethenyl)-2,6-dimethylphenyl]amino]-2-pyrimidinyl]amino]benzonitrile.

4-[[4-[[4-(2-cyanoethenyl)-2,6-dimethylphenyl]amino]-2-pyrimidinyl]amino]benzonitrile, in particular the E-isomer, has excellent HIV replication inhibiting activity against the wild type of HIV as well as drug and multi drug resistant strains of HIV (i.e. strains which have become resistant to art-known drug(s)). The compound has thus potential to be a good candidate for the development of a medicament for the treatment of HIV infection.

High pharmacological activity, a good pharmacological profile is however not the only factor which determines the drugability of a compound.

A good drug candidate should preferably also be stable chemically as well as physically; should have an acceptable toxicity profile; should have an acceptable bioavailability.

The bioavailability of the compound influences the dose of the compound required for administration in order to reach a therapeutically effective concentration of the compound in the patient. Compounds having a low bioavailability need to be administered in higher doses compared to compounds having a higher bioavailability. Possible consequences of the need for higher doses may comprise: an increased risk to adverse effects; an increase in the size of the dosage form; an increase in the frequency of administration. These factors may influence adherence to antiretroviral therapy.

Therapy adherence is one of the most important factors influencing the effectiveness of HIV treatment. Increase in dosing frequency and increase in pill size may lead to reduced therapy adherence and hence reduced therapy effectiveness.

Therefore, when designing a medicament for HIV treatment it is preferable to have an active compound with an acceptable bioavailability.

The bioavailability of a compound intended to be administered orally, is dependent on the compounds solubility in water as well as the compounds permeability (its ability to be absorbed across the intestinal membrane).

A scientific framework for classifying drug substances based on their aqueous solubility and intestinal permeability is the Biopharmaceutics Classification System or BCS. According to the BCS, drug substances are classified as follows:

Class 1: High Solubility-High Permeability
Class 2: Low Solubility-High Permeability
Class 3: High Solubility-Low Permeability
Class 4: Low Solubility-Low Permeability Compounds with a low solubility or a low permeability (class 2 to 4) may suffer from a low bioavailability when administered orally.

Free base 4-[[4-[[4-(2-cyanoethenyl)-2,6-dimethylphenyl]amino]-2-pyrimidinyl]amino]benzonitrile can be classified as a BCS class 2 compound and has thus a low solubility in water. 4-[[4-[[4-(2-cyanoethenyl)-2,6-dimethylphenyl]amino]-2-pyrimidinyl]amino]benzonitrile does not only exhibit a low solubility in water, but also in an acidic environment. Consequently, when administered orally in a conventional solid dosage form, a low bioavailability may be expected.

When confronted with a BCS class 2 compound intended for oral administration, a person skilled in pharmaceutical technology would turn to exploring possibilities for improving the compound's solubility, for instance by preparing an appropriate salt.

This route was also followed for 4-[[4-[[4-(2-cyanoethenyl)-2,6-dimethylphenyl]amino]-2-pyrimidinyl]amino]benzonitrile.

The prepared salts appeared to have only a slight improved solubility in water and in HCl. The prepared salts still belong to BCS class 2. Thus, also for the prepared salts a low bioavailability could be expected.

Unexpectedly, it has now been found that the hydrochloride salt of 4-[[4-[[4-(2-cyanoethenyl)-2,6-dimethylphenyl]amino]-2-pyrimidinyl]amino]benzonitrile, in particular its E-isomer, has a significant improved in vivo bioavailability compared to the free base. In fact, the present salt administered as a solid dosage form has an in vivo bioavailability which is comparable with the bioavailability of the free base administered as an oral PEG 400 solution.

Because of the increased bioavailability in vivo, the hydrochloride salt may be formulated without the need of complex formulation techniques.

The hydrochloride salt of the present invention was also found to be non-hygroscopic and to be chemically and physically stable in different conditions of humidity and temperatures.

DETAILED DESCRIPTION OF THE INVENTION

Figure 1:
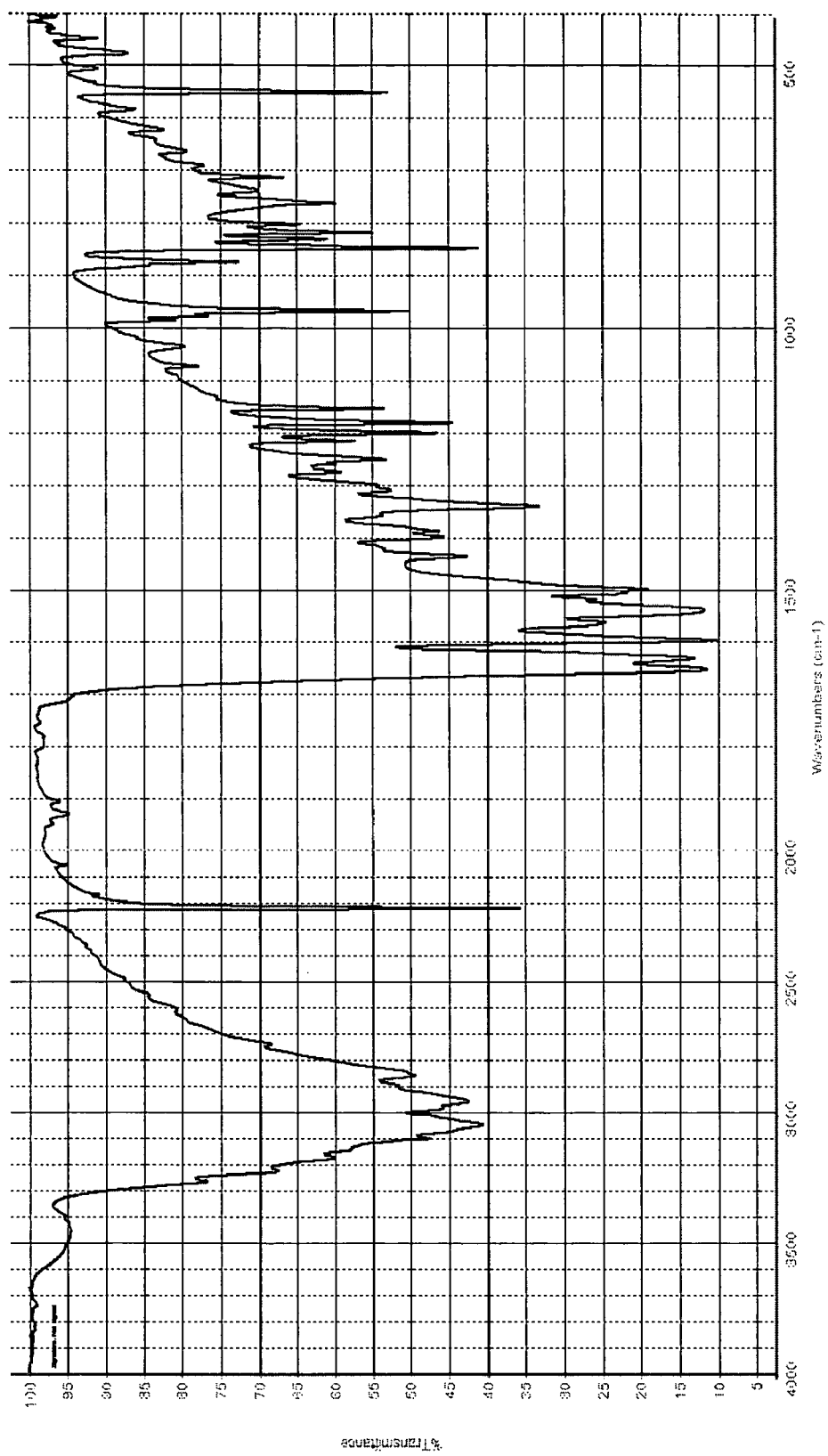
FIG. 1 is an IR spectrum of polymorphic Form A of (E) 4-[[4-[[4-(2-cyanoethenyl)-2,6-dimethylphenyl]amino]-2-pyrimidinyl]amino]benzonitrile. HCl

The present invention relates to the hydrochloride (HCl) salt of 4-[[4-[[4-(2-cyanoethenyl)-2,6-dimethylphenyl]amino]-2-pyrimidinyl]amino]benzonitrile, a N-oxide or a stereochemically isomeric form thereof.

Thus, the present invention relates in particular to a compound of formula (I)

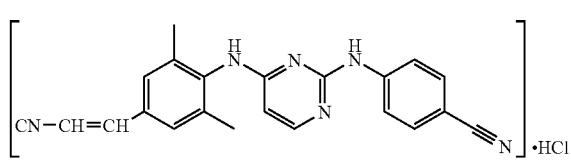

(I)

a N-oxide or a stereochemically isomeric form thereof.

The N-oxide forms of the present compound of formula (I) are meant to comprise the compounds of formula (I) wherein one or several tertiary nitrogen atoms are oxidized to the so-called N-oxide.

The term "stereochemically isomeric forms" as used hereinbefore defines all the possible stereoisomeric forms which the compound of formula (I), and the N-oxides may possess. Unless otherwise mentioned or indicated, the chemical designation of the compound denotes the mixture of all possible stereochemically isomeric forms as well as each of the individual isomeric forms of the compound of formula (I) and the N-oxides thereof substantially free of the other isomers. Stereochemically isomeric forms of the compound of formula (I) are obviously intended to be embraced within the scope of this invention.

The compound of formula (I) may exist in 2 stereochemical configurations at the double bond of the cyanoethenyl chain, i.e. the E (Entgegen) configuration (E-isomer) and the Z (Zusammen) configuration (Z isomer).

The terms E and Z are well known to a person skilled in the art.

A particular embodiment of the compound of formula (I) is the E-isomer, i.e. a compound of formula (I-a)

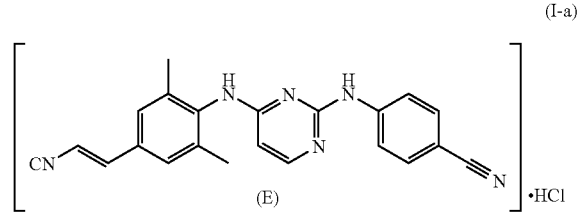

(I-a)

Another particular embodiment of the compound of formula (I) is the Z-isomer, i.e. a compound of formula (I-b)

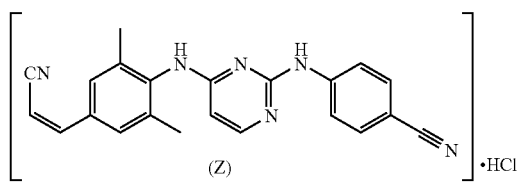

(I-b)

Whenever reference is made herein to the E-isomer, the pure E-isomer or any isomeric mixture of the E- and the Z-isomers wherein the E-isomer is predominantly present is meant, i.e. an isomeric mixture containing more than 50% or in particular more than 80% of the E-isomer, or even more in particular more than 90% of the E-isomer. Of particular interest is the E-isomer substantially free of the Z-isomer. Substantially free in this context refers to E-Z-mixtures with no or almost no Z-isomer, e.g. isomeric mixtures containing as much as 90%, in particular 95% or even 98% or 99% of the E-isomer.

Whenever reference is made herein to the Z-isomer, the pure Z-isomer or any isomeric mixture of the Z- and the E-isomers wherein the Z-isomer is predominantly present is meant, i.e. an isomeric mixture containing more than 50% or in particular more than 80% of the Z-isomer, or even more in particular more than 90% of the Z-isomer. Of particular interest is the Z-isomer substantially free of the E-isomer. Substantially free in this context refers to E-Z-mixtures with no or almost no E-isomer, e.g. isomeric mixtures containing as much as 90%, in particular 95% or even 98% or 99% of the Z-isomer.

Polymorphic forms of the present salts also fall within the ambit of the present invention.

Polymorphic forms of pharmaceutical compounds may be of interest to those involved in the development of a suitable dosage form because if the polymorphic form is not held constant during clinical and stability studies, the exact dosage used or measured may not be comparable from one lot to the next. Once a pharmaceutical compound is produced for use, it is important to recognize the polymorphic form delivered in each dosage form to assure that the production process use the same form and that the same amount of drug is included in each dosage. Therefore, it is imperative to assure that either a single polymorphic form or some known combination of polymorphic forms is present. In addition, certain polymorphic forms may exhibit enhanced thermodynamic stability and may be more suitable than other polymorpholic forms for inclusion in pharmaceutical formulations. As used herein, a polymorphic form of a compound of the invention is the same chemical entity, but in a different crystalline arrangement.

Solvent addition forms (solvates) which the salts of the present invention are able to form also fall within the ambit of the present invention. Examples of such forms are e.g. hydrates, alcoholates and the like. Solvates are herein also referred to as pseudopolymorphic forms. Preferred is an anhydric salt.

A particular embodiment of the present invention is a particular polymorphic or pseudopolymorphic form of a compound of formula (I-a), i.e. (E) 4-[[4-[[4-(2-cyanoethenyl)-2,6-dimethylphenyl]amino]-2-pyrimidinyl]amino] benzonitrile.HCl.

Figure 2:
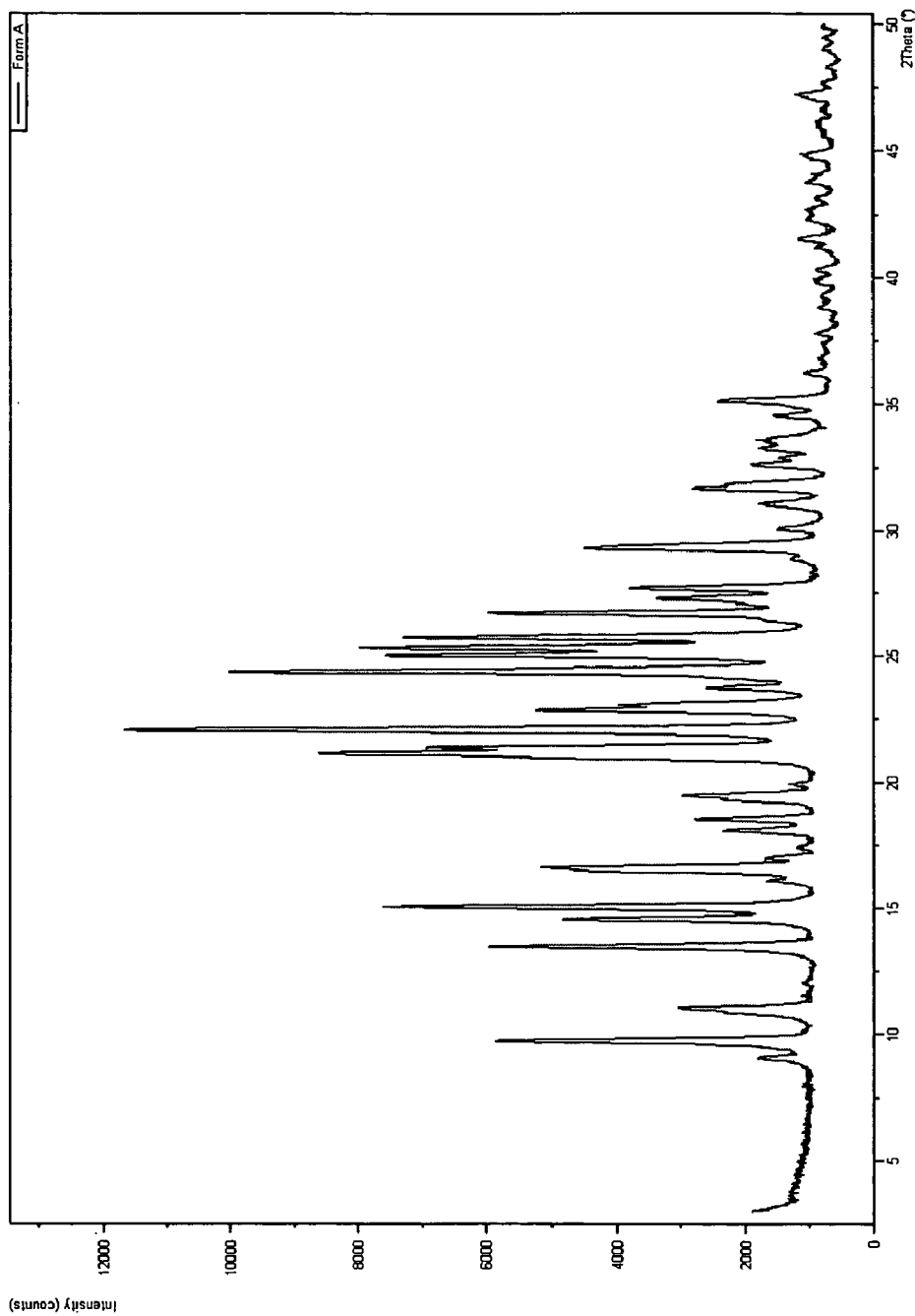
FIG. 2 is X-ray powder diffraction pattern of polymorphic Form A of (E) 4-[[4-[[4-(2-cyanoethenyl)-2,6-dimethylphenyl]amino]-2-pyrimidinyl]amino]benzonitrile. HCl.

A first particular polymorphic form of the compound of formula (I-a) is herein designated as Form A (see FIGS. 1 and 2).

Figure 3:
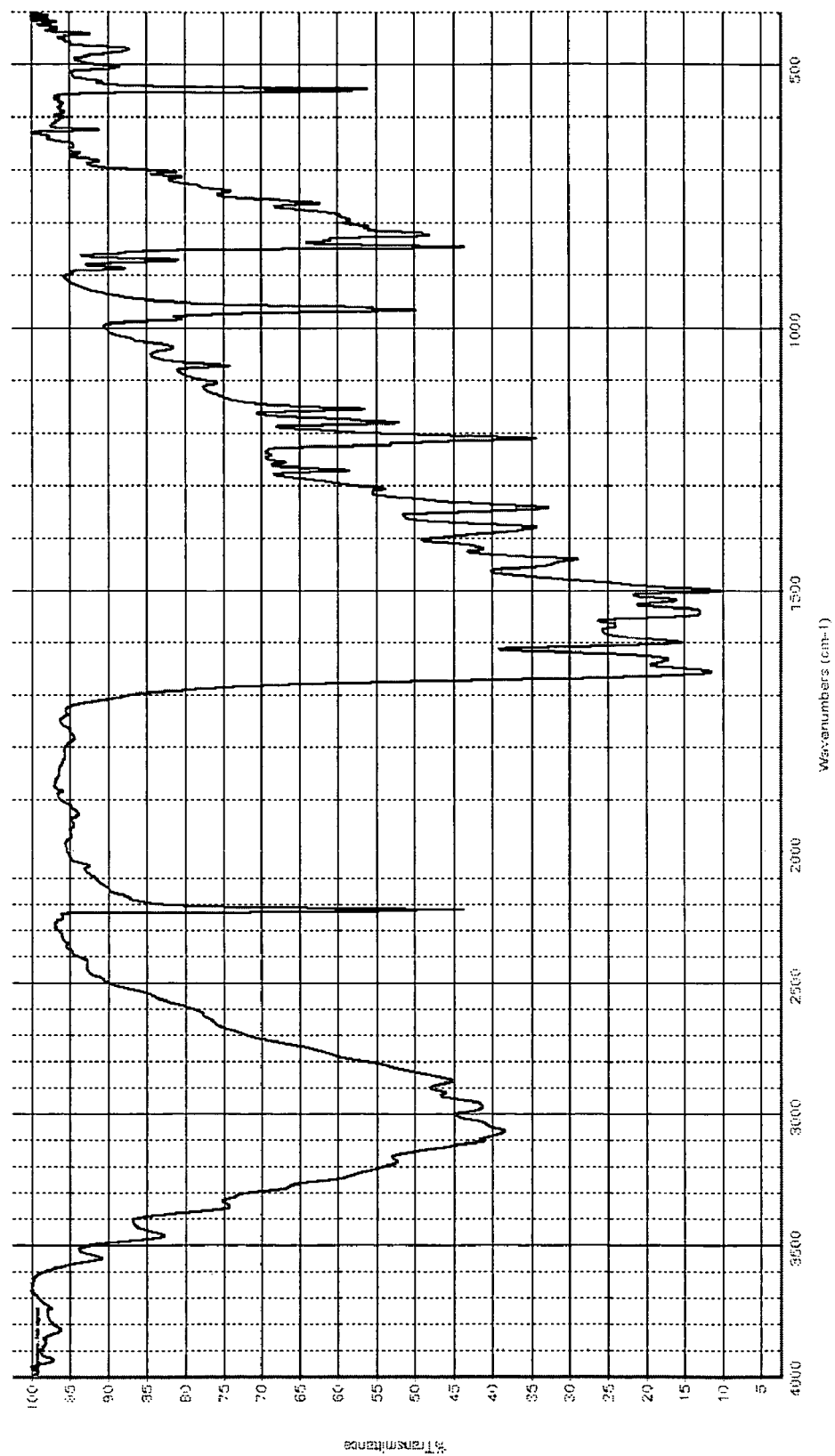
FIG. 3 is an IR spectrum of the dry state of polymorphic Form B of (E) 4-[[4-[[4-(2-cyanoethenyl)-2,6-dimethylphenyl]amino]-2-pyrimidinyl]amino]benzonitrile. HCl
Figure 4:
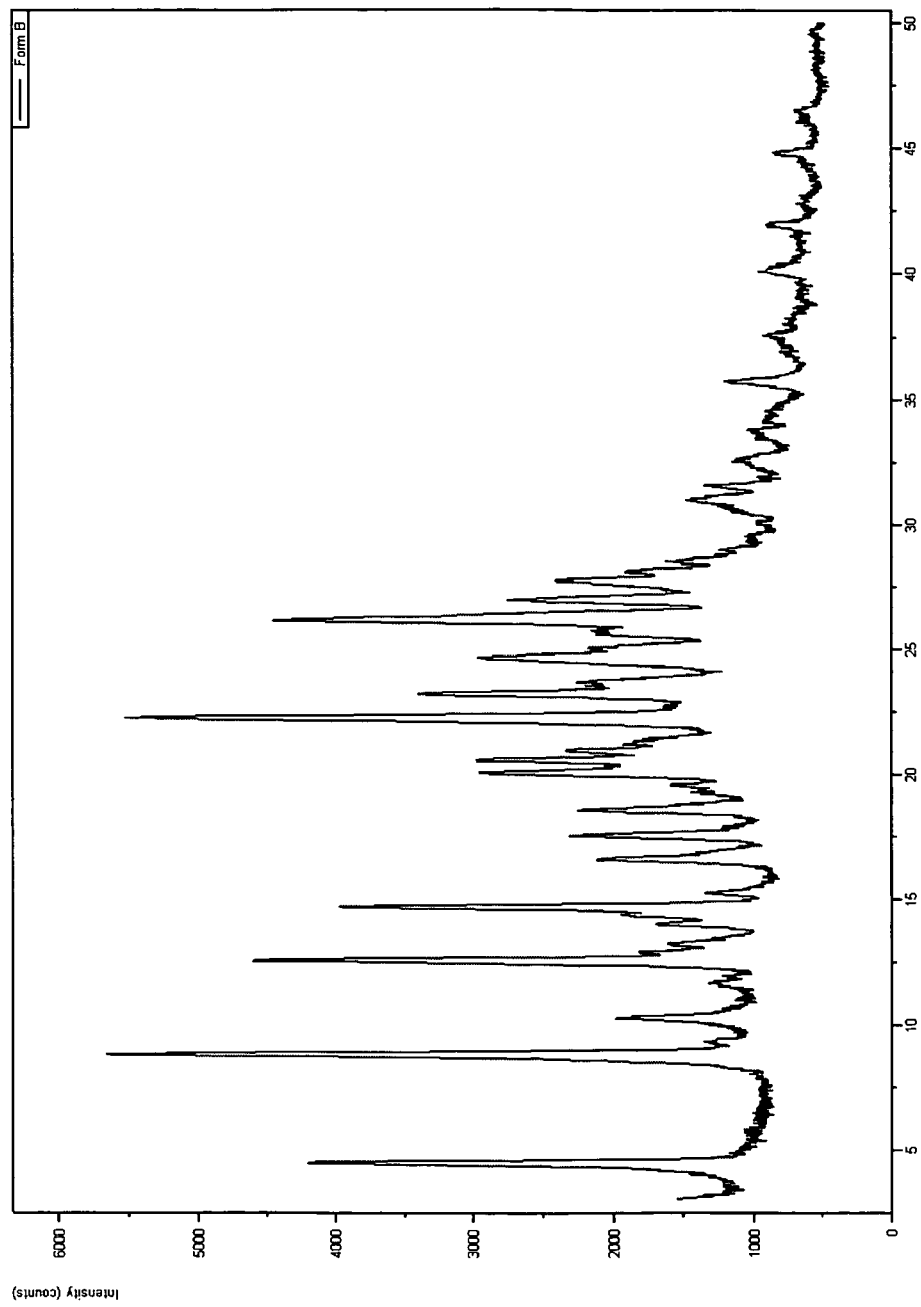
FIG. 4 is X-ray powder diffraction pattern of the dry state of polymorphic Form B of (E) 4-[[4-[[4-(2-cyanoethenyl)-2,6-dimethylphenyl]amino]-2-pyrimidinyl]amino]benzonitrile. HCl.

A second particular form of the compound of formula (I-a) is herein designated as Form B. Form B can be present in two states, a dry state (polymorphic form) and a wetted state (pseudopolymorphic form). Only the characteristics of form B in the dry state are given (see FIGS. 3 and 4).

Figure 5:
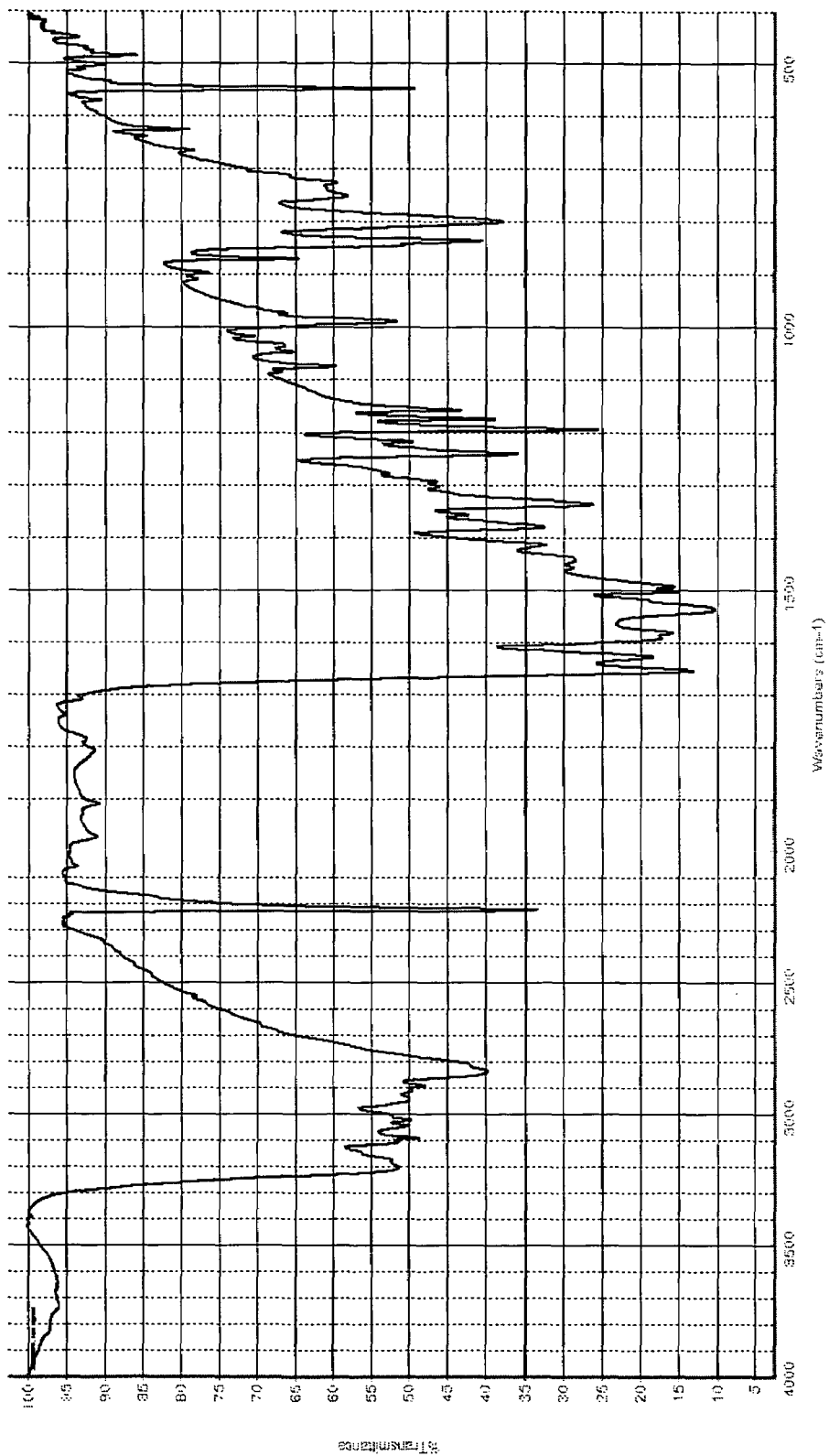
FIG. 5 is an IR spectrum of polymorphic Form C of (E) 4-[[4-[[4-(2-cyanoethenyl)-2,6-dimethylphenyl]amino]-2-pyrimidinyl]amino]benzonitrile. HCl
Figure 6:
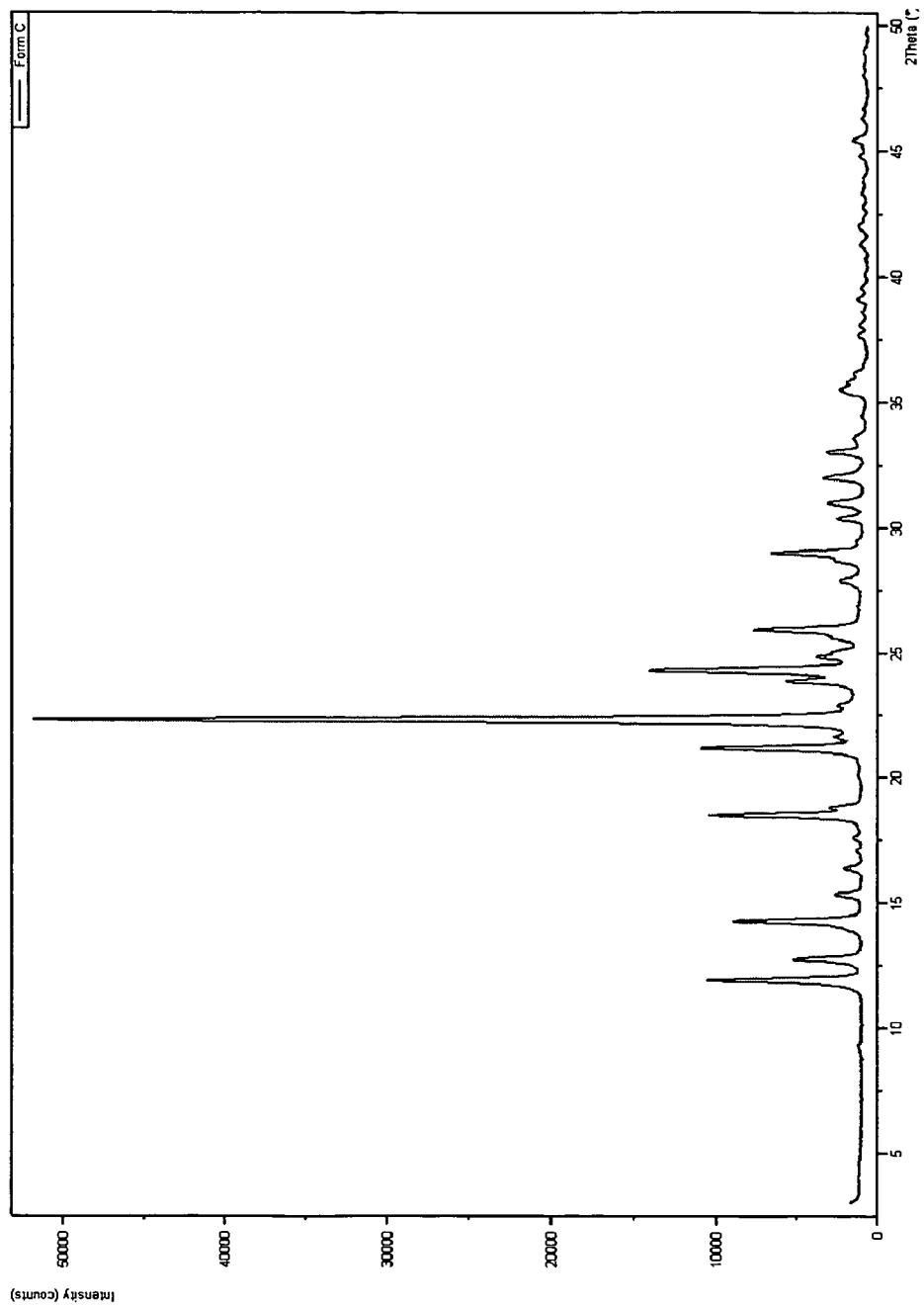
FIG. 6 is X-ray powder diffraction pattern of polymorphic Form C of (E) 4-[[4-[[4-(2-cyanoethenyl)-2,6-dimethylphenyl]amino]-2-pyrimidinyl]amino]benzonitrile. HCl.

A third particular polymorphic form of the compound of formula (I-a) is herein designated as Form C (see FIGS. 5 and 6).

Figure 7:
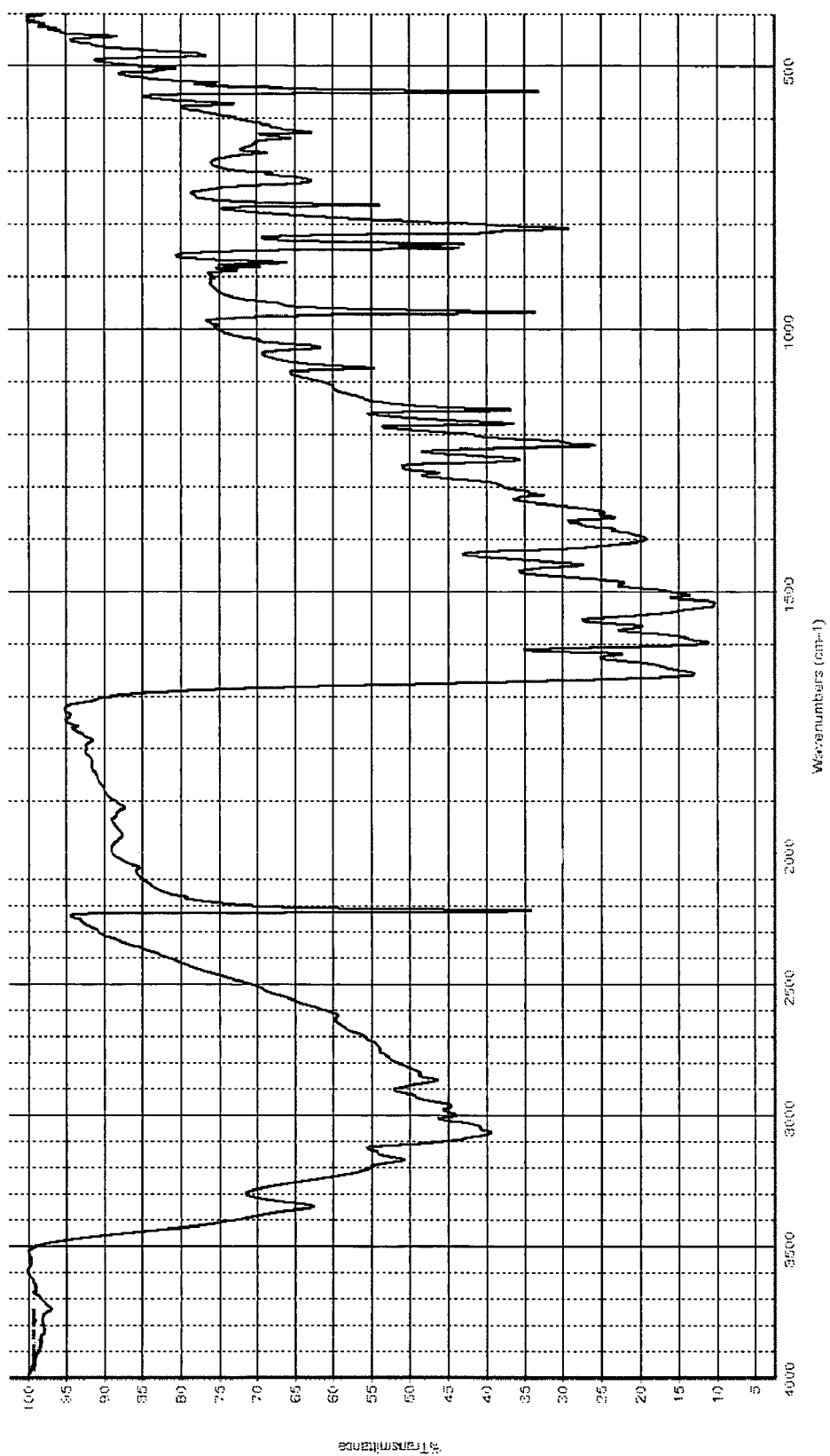
FIG. 7 is an IR spectrum of pseudopolymorphic Form D of (E) 4-[[4-[[4-(2-cyanoethenyl)-2,6-dimethylphenyl]amino]-2-pyrimidinyl]amino]benzonitrile. HCl
Figure 8:
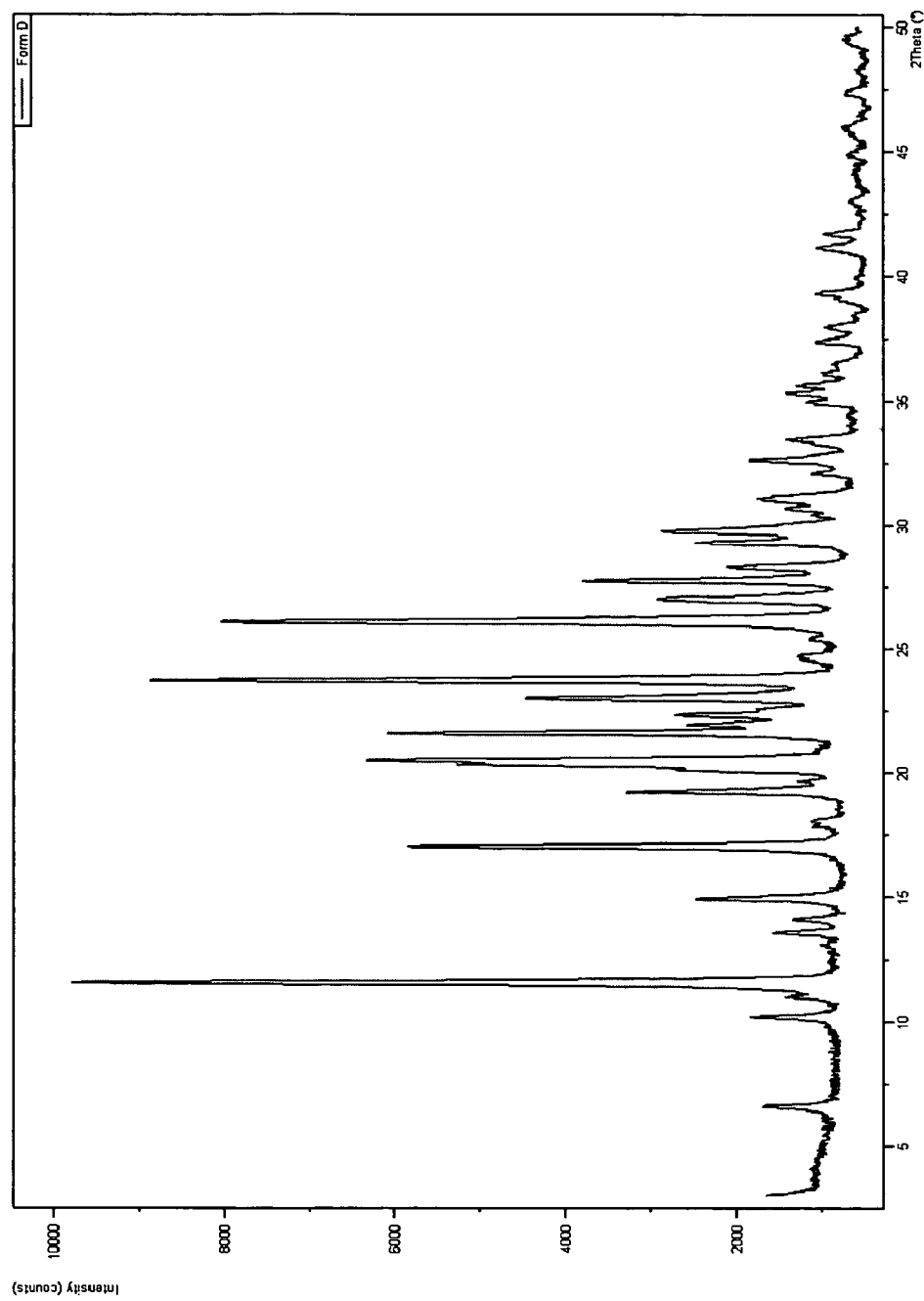
FIG. 8 is X-ray powder diffraction pattern of pseudopolymorphic Form D of (E) 4-[[4-[[4-(2-cyanoethenyl)-2,6-dimethylphenyl]amino]-2-pyrimidinyl]amino]benzonitrile. HCl.

A fourth particular pseudopolymorphic form of the compound of formula (I-a) is herein designated as Form D (see FIGS. 7 and 8).

A preferred polymorphic form of the compound of formula (I-a) is Form A.

Whenever used hereinafter, the term "compound of formula (I), (I-a) or (I-b)" is meant to also include the N-oxide forms, the stereochemically isomeric forms and the polymorphic or pseudopolymorphic forms. Of special interest is a stereochemically pure form of the compound of formula (I). A preferred compound of formula (I) is a compound of formula (I-a).

The compounds of formula (I), (I-a) or (I-b) can be prepared by reacting the corresponding free base with hydrochloric acid (HCl) in the presence of a suitable solvent, such as for example a suitable acid, e.g. acetic acid.

The compounds of formula (I), (I-a) or (I-b) have antiretroviral activity. They are able to inhibit the replication of HIV, in particular HIV-1. HIV (Human Immunodeficiency Virus) is the aetiological agent of Acquired Immune Deficiency Syndrome (AIDS) in humans. The HIV virus preferentially infects human T-4 cells and destroys them or changes their normal function, particularly the coordination of the immune system. As a result, an infected patient has an ever decreasing number of T-4 cells, which moreover behave abnormally. Hence, the immunological defense system is unable to combat infections and neoplasms and the HIV infected subject usually dies by opportunistic infections such as pneumonia, or by cancers. Other conditions associated with HIV infection include thrombocytopaenia, Kaposi's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy (PGL) and AIDS-related complex (ARC).

The present compounds also show activity against drug and multidrug resistant HIV strains, in particular drug and multidrug resistant HIV-1 strains, more in particular the present compounds show activity against HIV strains, especially HIV-1 strains, that have acquired resistance to one or more art-known non-nucleoside reverse transcriptase inhibitors. Art-known non-nucleoside reverse transcriptase inhibitors are those non-nucleoside reverse transcriptase inhibitors other than the present compounds and in particular commercial non-nucleoside reverse transcriptase inhibitors..

The HIV replication inhibiting activity of 4-[[4-[[4-(2-cyanoethenyl)-2,6-dimethylphenyl]amino]-2-pyrimidinyl]amino]benzonitrile is described in WO 03/16306, which is incorporated herein by reference.

Due to their antiretroviral properties, particularly their anti-HIV properties, especially their HIV-1 replication inhibiting activity, the present compounds are useful in the treatment of individuals infected by HIV and for the prophylaxis of these infections. In general, the compounds of the present invention may be useful in the treatment of warm-blooded mammals infected with viruses whose existence is mediated by, or depends upon, the enzyme reverse transcriptase. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic Central Nervous System diseases caused by retroviruses, such as, for example HIV mediated dementia and multiple sclerosis Therefore, the compounds of formula (I), (I-a) or (I-b) can be used as a medicine.

The compounds of the present invention may therefore be used as medicines against above-mentioned conditions. Said use as a medicine or method of treatment comprises the administration to HIV-infected subjects of an amount effective to combat the conditions associated with HIV and other pathogenic retroviruses, especially HIV-1. In particular, the present compounds may be used in the manufacture of a medicament for the treatment or the prevention of HIV infection, preferably for the treatment of HIV infection.

In view of the utility of the present compounds, there is also provided a method of treating mammals, including humans, suffering from or a method of preventing warm-blooded mammals, including humans, to suffer from viral infections, especially HIV infections. Said method comprises the administration, preferably oral administration, of an effective amount of a salt of the present invention to mammals including humans.

Due to the higher bioavailability of the present compounds compared to the corresponding free base, therapeutic effective plasma levels may be obtained by administering a pharmaceutical composition comprising a lower amount of the salt compared to what would be needed of the corresponding free base.

Therefore, the size of the pharmaceutical composition may be reduced or the frequency of dosing may be reduced.

Thus, the present invention also relates to a pharmaceutical composition comprising a pharmaceutically acceptable carrier and as active ingredient a therapeutically effective amount of a compound of formula (I), (I-a) or (I-b).

The present invention also relates to a pharmaceutical composition comprising a pharmaceutically acceptable carrier and as active ingredient a therapeutically effective amount of a compound of formula (I), (I-a) or (I-b).

In particular, the present invention also relates to a pharmaceutical composition comprising a pharmaceutically acceptable carrier and as active ingredient a therapeutically effective amount of a compound of formula (I), (I-a) or (I-b).

The present compounds of formula (I), (I-a) or (I-b) may be formulated into various pharmaceutical compositions for administration purposes. As appropriate compositions there may be cited all compositions usually employed for systemically administering drugs. To prepare the pharmaceutical compositions of this invention, an effective amount of the compound of formula (I), (I-a) or (I-b) as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral unit dosage forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations, which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The salts of the present invention may also be administered via inhalation or insufflation by means of methods and formulations employed in the art for administration via this way. Thus, in general the salts of the present invention may be administered to the lungs in the form of a solution, a suspension or a dry powder. Any system developed for the delivery of solutions, suspensions or dry powders via oral or nasal inhalation or insufflation are suitable for the administration of the present compounds.

The compounds of the present invention may also be topically administered in the form of drops, in particular eye drops. Said eye drops may be in the form of a solution or a suspension. Any system developed for the delivery of solutions or suspensions as eye drops are suitable for the administration of the present compounds.

WO 2004/069812 which is incorporated herein by reference, describes the ability of pyrimidine derivatives among which 4-[[4-[[4-(2-cyanoethenyl)-2,6-dimethylphenyl]amino]-2-pyrimidinyl]amino]benzonitrile and pharmaceutically acceptable salts thereof, to prevent HIV infection via sexual intercourse or related intimate contact between partners. Therefore, the present invention also relates to a pharmaceutical composition in a form adapted to be applied to a site where sexual intercourse or related intimate contact can take place, such as the genitals, rectum, mouth, hands, lower abdomen, upper thighs, especially the vagina and mouth, comprising a pharmaceutically acceptable carrier and as active ingredient an effective amount of a compound of formula (I), (I-a) or (I-b). In particular to a pharmaceutical composition in a form adapted to be applied to a site where sexual intercourse or related intimate contact can take place, such as the genitals, rectum, mouth, hands, lower abdomen, upper thighs, especially the vagina and mouth, comprising a pharmaceutically acceptable carrier and as active ingredient an effective amount of a compound of formula (I), (I-a) or (I-b). More in particular, the present invention also relates to a pharmaceutical composition in a form adapted to be applied to a site where sexual intercourse or related intimate contact can take place, such as the genitals, rectum, mouth, hands, lower abdomen, upper thighs, especially the vagina and mouth, comprising a pharmaceutically acceptable carrier and as active ingredient an effective amount of a compound of formula (I), (I-a) or (I-b). As appropriate special adapted compositions there may be cited all compositions usually employed for being applied to the vagina, rectum, mouth and skin such as for example gels, jellies, creams, ointments, films, sponges, foams, intravaginal rings, cervical caps, suppositories for rectal or vaginal application, vaginal or rectal or buccal tablets, mouthwashes. To prepare such pharmaceutical compositions, an effective amount of the active ingredient is combined in intimate admixture with a pharmaceutically acceptable carrier, which carrier may take a wide variety of forms depending on the form of administration. In order to increase the residence time of such pharmaceutical composition at the site of administration, it may be advantageous to include in the composition a bioadhesive, in particular a bioadhesive polymer. A bioadhesive may be defined as a material that adheres to a live biological surface such as for example a mucus membrane or skin tissue.

Thus, the present invention also relates to a pharmaceutical composition comprising a pharmaceutically acceptable carrier and as active ingredient an effective amount of a compound of formula (I), (I-a) or (I-b) characterized in that the pharmaceutical composition is bioadhesive to the site of application. Preferably, the site of application is the vagina, rectum, mouth or skin, most preferred is the vagina.

In particular, the present invention also relates to a pharmaceutical composition comprising a pharmaceutically acceptable carrier and as active ingredient an effective amount of a compound of formula (I), (I-a) or (I-b) characterized in that the pharmaceutical composition is bioadhesive to the site of application. More in particular, the present invention also relates to a pharmaceutical composition comprising a pharmaceutically acceptable carrier and as active ingredient an effective amount of a compound of formula (I), (I-a) or (I-b) characterized in that the pharmaceutical composition is bioadhesive to the site of application.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The exact dosage and frequency of administration depends on the particular condition being treated, the severity of the condition being treated, the age, weight, sex, extent of disorder and general physical condition of the particular patient as well as other medication the individual may be taking, as is well known to those skilled in the art.

Furthermore, it is evident that said effective daily amount may be lowered or increased depending on the response of the treated subject and/or depending on the evaluation of the physician prescribing the compounds of the instant invention.

The pharmaceutical compositions of the present invention can be administered at any time of the day independently of the food taken in by the subject. Preferably, the present compositions are administered to fed subjects.

An interesting embodiment of the present invention concerns an oral pharmaceutical composition, i.e. a pharmaceutical composition suitable for oral administration, comprising a pharmaceutically acceptable carrier and as active ingredient a therapeutically effective amount of a compound of formula (I), (I-a) or (I-b). In particular, the present invention concerns an oral pharmaceutical composition, i.e. a pharmaceutical composition suitable for oral administration, comprising a pharmaceutically acceptable carrier and as active ingredient a therapeutically effective amount of a compound of formula (I), (I-a) or (I-b), more in particular a pharmaceutical composition suitable for oral administration, comprising a pharmaceutically acceptable carrier and as active ingredient a therapeutically effective amount of a compound of formula (I), (I-a) or (I-b).

In particular, the oral pharmaceutical composition is a solid oral pharmaceutical composition, more in particular a tablet or a capsule, even more in particular a tablet. A tablet according to the present invention may be formulated as a once daily tablet.

Preferably, the pharmaceutical compositions of the present invention contain those quantities of a compound of formula (I), (I-a) or (I-b) equivalent to from about 5 to about 500 mg of the corresponding free base 4-[[4-[[4-(2-cyanoethenyl)-2, 6-dimethylphenyl]amino]-2-pyrimidinyl]amino]benzonitrile, its E or Z isomer, more preferably from about 10 mg to about 250 mg of the corresponding free base, even more preferably from about 20 mg to about 200 mg of the corresponding free base. Preferably, the present pharmaceutical compositions contain those quantities of a compound of formula (I), (I-a) or (I-b) equivalent to 25 mg, 50 mg, 75 mg, 100 mg or 150 mg of the corresponding free base (base equivalent).

As used hereinbefore or hereinafter, the term "about" in relation to a numerical value x means, for example, x±10%.

The particle size of the compound of formula (I), (I-a) or (I-b) preferably is less than 50 µm, more preferably less than 25 µm, even more preferably less than 20 µm. Further preferred is a particle size of about 15 µm or less, or about 12 µm or less, or about 10 µm or less, or about 5 µm or less. Most preferably, the particle size ranges between about 0.2 and about 15 µm or between about 0.2 and about 10 µm.

The pharmaceutical compositions of the present invention preferably comprise a wetting agent.

As for the wetting agent in the compositions of the invention, there may be used any of the physiologically tolerable wetting agent suitable for use in a pharmaceutical composition.

It is well-known in the art that a wetting agent is an amphiphilic compound; it contains polar, hydrophilic moieties as well as non-polar, hydrophobic moieties.

The terms "hydrophilic" or "hydrophobic" are relative terms.

The relative hydrophilicity or hydrophobicity of a wetting agent may be expressed by its hydrophilic-lipophilic balance value ("HLB value). Wetting agents with a lower HLB value are catagorized as being "hydrophobic" wetting agents whereas wetting agents with a higher HLB value are catagorized as being "hydrophilic" wetting agents. As a rule of thumb, wetting agents having a HLB value greater than about 10 are generally considered as being hydrophilic wetting agents; wetting agents having a HLB value lower than about 10 are generally considered as being hydrophobic wetting agents.

The present compositions preferably comprise a hydrophilic wetting agent.

It should be appreciated that the HLB value of a wetting agent is only a rough guide to indicate the hydrophilicity/hydrophobicity of a wetting agent. The HLB value of a particular wetting agent may vary depending upon the method used to determine the HLB value; may vary depending on its commercial source; is subject to batch to batch variability. A person skilled in the art can readily identify hydrophilic wetting agents suitable for use in the pharmaceutical compositions of the present invention.

The wetting agent of the present invention can be an anionic, a cationic, a zwitterionic or a non-ionic wetting agent, the latter being preferred. The wetting agent of the present invention can also be a mixture of two or more wetting agents.

Suitable wetting agents for use in the compositions of the present invention are listed below. It should be emphasized that said list of wetting agents is only illustrative, representative and not exhaustive. Thus the invention is not limited to the wetting agents listed below. In the present compositions, also mixtures of wetting agents may be used.

Suitable wetting agents which may be used in the present invention comprise:

a) Polyethylene glycol fatty acid monoesters comprising esters of lauric acid, oleic acid, stearic acid, ricinoic acid and the like with PEG 6, 7, 8, 9, 10, 12, 15, 20, 25, 30, 32, 40, 45, 50, 55, 100, 200, 300, 400, 600 and the like, for instance PEG-6 laurate or stearate, PEG-7 oleate or laurate, PEG-8 laurate or oleate or stearate, PEG-9 oleate or stearate, PEG-10 laurate or oleate or stearate, PEG-12 laurate or oleate or stearate or ricinoleate, PEG-15 stearate or oleate, PEG-20 laurate or oleate or stearate, PEG-25 stearate, PEG-32 laurate or oleate or stearate, PEG-30 stearate, PEG-40 laurate or oleate or stearate, PEG-45 stearate, PEG-50 stearate, PEG-55 stearate, PEG-100 oleate or stearate, PEG-200 oleate, PEG-400 oleate, PEG-600 oleate; (the wetting agents belonging to this group are for instance known as Cithrol, Algon, Kessco, Lauridac, Mapeg, Cremophor, Emulgante, Nikkol, Myrj, Crodet, Albunol, Lactomul)

b) Polyethylene glycol fatty acid diesters comprising diesters of lauric acid, stearic acid, palmic acid, oleic acid and the like with PEG-8, 10, 12, 20, 32, 400 and the like, for instance PEG-8 dilaurate or distearate, PEG-10 dipalmitate, PEG-12 dilaurate or distearate or dioleate, PEG-20 dilaurate or distearate or dioleate PEG-32 dilaurate or distearate or dioleate, PEG-400 dioleate or distearate; (the wetting agents belonging to this group are for instance known as Mapeg, Polyalso, Kessco, Cithrol)

c) Polyethylene glycol fatty acid mono-and diester mixtures such as for example PEG 4-150 mono and dilaurate, PEG 4-150 mono and dioleate, PEG 4-150 mono and distearate and the like; (the wetting agents belonging to this group are for instance known as Kessco)

d) Polyethylene glycol glycerol fatty acid esters such as for instance PEG-20 glyceryl laurate or glyceryl stearate or glyceryl oleate, PEG-30 glyceryl laurate or glyceryl oleate, PEG-15 glyceryl laurate, PEG-40 glyceryl laurate and the like; (the wetting agents belonging to this group are for instance known as Tagat, Glycerox L, Capmul), e) Alcohol-oil transesterification products comprising esters of alcohols or polyalcohols such as glycerol, propylene glycol, ethylene glycol, polyethylene glycol, sorbitol, pentaerythritol and the like with natural and/or hydrogenated oils or oil-soluble vitamins such as castor oil, hydrogenated castor oil, vitamin A, vitamin D, vitamin E, vitamin K, an edible vegetable oil e.g. corn oil, olive oil, peanut oil, palm kernel oil, apricot kernel oil, almond oil and the like, such as PEG-20 castor oil or hydrogenated castor oil or corn glycerides or almond glycerides, PEG-23 castor oil, PEG-25 hydrogenated castor oil or trioleate, PEG-35 castor oil, PEG-30 castor oil or hydrogenated castor oil, PEG-38 castor oil, PEG-40 castor oil or hydrogenated castor oil or palm kernel oil, PEG-45 hydrogenated castor oil, PEG-50 castor oil or hydrogenated castor oil, PEG-56 castor oil, PEG-60 castor oil or hydrogenated castor oil or corn glycerides or almond glycerides, PEG-80 hydrogenated castor oil, PEG-100 castor oil or hydrogenated castor oil, PEG-200 castor oil, PEG-8 caprylic/capric glycerides, PEG-6 caprylic/capric glycerides, lauroyl macrogol-32 glyceride, stearoyl macrogol glyceride, tocopheryl PEG-1000 succinate (TPGS); (the wetting agents belonging to this group are for instance known as Emalex, Cremophor, Emulgante, Eumulgin, Nikkol, Thornley, Simulsol, Cerex, Crovol, Labrasol, Softigen, Gelucire, Vitamin E TPGS), f) polyglycerized fatty acids comprising polyglycerol esters of fatty acids such as for instance polyglyceryl-10 laurate or oleate or stearate, polyglyceryl-10 mono and dioleate, polyglyceryl polyricinoleate and the like; (the wetting agents belonging to this group are for instance known as Nikkol Decaglyn, Caprol or Polymuls)

g) Sterol derivatives comprising polyethylene glycol derivatives of sterol such as PEG-24 cholesterol ether, PEG-30 cholestanol, PEG-25 phyto sterol, PEG-30 soya sterol and the like; (the wetting agents belonging to this group are for instance known as Solulan™ or Nikkol BPSH)

h) Polyethylene glycol sorbitan fatty acid esters such as for example PEG-10 sorbitan laurate, PEG-20 sorbitan monolaurate or sorbitan tristearate or sorbitan monooleate or sorbitan trioleate or sorbitan monoisostearate or sorbitan monopalmiate or sorbitan monostearate, PEG-4 sorbitan monolaurate, PEG-5 sorbitan monooleate, PEG-6 sorbitan monooleate or sorbitan monolaurate or sorbitan monostearate, PEG-8 sorbitan monostearate, PEG-30 sorbitan tetraoleate, PEG-40 sorbitan oleate or sorbitan tetraoleate, PEG-60 sorbitan tetrastearate, PEG-80 sorbitan monolaurate, PEG sorbitol hexaoleate (Atlas G-1086) and the like; (the wetting agents belonging to this group are for instance known as Liposorb, Tween, Dacol MSS, Nikkol, Emalex, Atlas)

i) Polyethylene glycol alkyl ethers such as for instance PEG-10 oleyl ether or cetyl ether or stearyl ether, PEG-20 oleyl ether or cetyl ether or stearyl ether, PEG-9 lauryl ether, PEG-23 lauryl ether (laureth-23), PEG-100 stearyl ether and the like; (the wetting agents belonging to this group are for instance known as Volpo, Brij)

j) Sugar esters such as for instance sucrose distearate/monostearate, sucrose monostearate or monopalmitate or monolaurate and the like; (the wetting agents belonging to this group are for instance known as Sucro ester, Crodesta, Saccharose monolaurate)

k) Polyethylene glycol alkyl phenols such as for instance PEG-10-100 nonyl phenol (Triton X series), PEG-15-100 ocyl phenol ether (Triton N series) and the like;

l) Polyoxyethylene-polyoxypropylene block copolymers (poloxamers) such as for instance poloxamer 108, poloxamer 188, poloxamer 237, poloxamer 288 and the like; (the wetting agents belonging to this group are for instance known as Synperonic PE, Pluronic, Emkalyx, Lutrol™, Supronic, Monolan, Pluracare, Plurodac)

m) ionic wetting agents including cationic, anionic and zwitterionic surfactans such as the fatty acid salts e.g. sodium oleate, sodium lauryl sulfate, sodium lauryl sarcosinate, sodium dioctyl sulfosuccinate, sodium myristate, sodium palmitate, sodium state, sodium ricinoleate and the like; such as bile salts e.g. sodium cholate, sodium taurocholate, sodium glycocholate and the like; such as phospholipids e.g. egg/soy lecithin, hydroxylated lecithin, lysophosphatidylcholine, phosphatidylcholine, phosphatidyl ethanolamine, phosphatidyl glycerol, phosphatidyl serine and the like; such as phosphoric acid esters e.g. diethanolammonium polyoxyethylene-10 oleyl ether phosphate, esterification products of fatty alcohols or fatty alcohol ethoxylates with phosphoric acid or anhydride; such as carboxylates e.g. succinylated monoglycerides, sodium stearyl fumarate, stearoyl propylene glycol hydrogen succinate, mono/diacetylated tartaric acid esters of mono-and diglycerides, citric acid esters of mono- and diglycerides, glyceryl-lacto esters of fatty acids, lactylic esters of fatty acids, calcium/sodium stearoyl-2-lactylate, calcium/sodium stearoyl lactylate, alginate salts, propylene glycol alginate, ether carboxylates and the like; such as sulfates and sulfonates e.g. ethoxylated alkyl sulfates, alkyl benzene sulfates, alpha-olefin sulfonates, acyl isethionates, acyl taurates, alkyl glyceryl ether sulfonates, octyl sulfosuccinate disodium, disodium undecyleneamido-MEA-sulfosuccinate and the like; such as cationic wetting agents e.g. hexadecyl triammonium bromide, decyl trimethyl ammonium bromide, cetyl trimethyl ammonium bromide, dodecyl ammonium chloride, alkyl benzyldimethylammonium salts, diisobutyl phenoxyethoxydimethyl benzylammonium salts, alkylpyridinium salts, betaines (lauryl betaine), ethoxylated amines (polyoxyethylene-15 coconut amine) and the like.

When in the above list of suitable wetting agents, different possibilities are listed such as for example PEG-20 oleyl ether or cetyl ether or stearyl ether, this means that PEG-20 oleyl ether and PEG-20 cetyl ether and PEG-20 stearyl ether are intended. Thus for instance PEG-20 castor oil or hydrogenated castor oil or corn glycerides or almond glycerides has to be read as PEG-20 castor oil and PEG-20 hydrogenated castor oil and PEG-20 corn glycerides and PEG-20 almond glycerides.

Preferred wetting agents in the present compositions are sodium lauryl sulfate, sodium dioctyl sulfosuccinate, or those wetting agents belonging to the group of the polyethylene glycol sorbitan fatty acid esters, such as wetting agents known as Tween, e.g. Tween 20, 60, 80. Most preferred, the wetting agent is Tween 20.

In the compositions of the invention, the wetting agent is preferably present at a concentration from about 0.01 to about 5% by weight relative to the total weight of the composition, preferably from about 0.1 to about 3% by weight, more preferably from about 0.1 to about 1% by weight.

The quantity of wetting agent used in the present compositions may depend on the amount of the compound of formula (I), (I-a) or (I-b) present in the composition or on the particle size of the compound of formula (I), (I-a) or (I-b). A higher amount or a smaller particle size may require more wetting agent.

In case of a solid oral pharmaceutical composition according to the present invention, such as a tablet or a capsule, the composition may also further contain an organic polymer.

The organic polymer may be used as a binder during the manufacture of the composition.

The organic polymer used in the compositions of the invention may be any of the physiologically tolerable water soluble synthetic, semi-synthetic or non-synthetic organic polymers.

Thus for example the polymer may be a natural polymer such as a polysaccharide or polypeptide or a derivative thereof, or a synthetic polymer such as a polyalkylene oxide (e.g. PEG), polyacrylate, polyvinylpyrrolidone, etc. Mixed polymers, e.g. block copolymers and glycopeptides may of course also be used.

The polymer conveniently has a molecular weight in the range 500D to 2 MD, and conveniently has an apparent viscosity of 1 to 15,000 mPa·s when in a 2% aqueous solution at 20° C. For example, the water-soluble polymer can be selected from the group comprising alkylcelluloses such as methylcellulose, hydroxyakylcelluloses such as hydroxymethylcellulose, hydroxyethylcellulose, hydroxypropylcellulose and hydroxybutylcellulose, hydroxyalkyl alkylcelluloses such as hydroxyethyl methylcellulose and hydroxypropyl methylcellulose (e.g. HPMC 2910 15 mPa·s; HPMC 2910 5 mPa·s), carboxyalkylcelluloses such as carboxymethylcellulose, alkali metal salts of carboxyalkylcelluloses such as sodium carboxymethylcellulose,
carboxyalkylalkylcelluloses such as carboxymethylethylcellulose,
carboxyalkylcellulose esters,
starches, such as starch 1551,
pectins such as sodium carboxymethylamylopectin,
chitin derivates such as chitosan,
heparin and heparinoids,
polysaccharides such as alginic acid, alkali metal and ammonium salts thereof, carrageenans, galactomannans, tragacanth, agar-agar, gum arabic, guargum and xanthan gum,
polyacrylic acids and the salts thereof,
polymethacrylic acids and the salts thereof, methacrylate copolymers,
polyvinylalcohol,
polyvinylpyrrolidone, copolymers of polyvinylpyrrolidone with vinyl acetate,
polyalkylene oxides such as polyethylene oxide and polypropylene oxide and copolymers of ethylene oxide and propylene oxide, e.g. poloxamers and poloxamines.

Non-enumerated polymers which are pharmaceutically acceptable and have appropriate physico-chemical properties as defined hereinbefore are equally suited for preparing compositions according to the present invention.

Preferably the organic polymer is starch, polyvinylpyrrolidone or a cellulose ether, e.g. PVP K29-32, PVP K90, methyl cellulose, hydroxypropylcellulose, hydroxyethyl methylcellulose, or hydroxypropyl methylcellulose (HPMC).

Said HPMC contains sufficient hydroxypropyl and methoxy groups to render it water-soluble. HPMC having a methoxy degree of substitution from about 0.8 to about 2.5 and a hydroxypropyl molar substitution from about 0.05 to about 3.0 are generally water-soluble. Methoxy degree of substitution refers to the average number of methyl ether groups present per anhydroglucose unit of the cellulose molecule. Hydroxypropyl molar substitution refers to the average number of moles of propylene oxide which have reacted with each anhydroglucose unit of the cellulose molecule. A preferred HPMC is hypromellose 2910 15 mPa·s or hypromellose 2910 5 mPa·s, especially hypromellose 2910 15 mPa·s. Hydroxypropyl methylcellulose is the United States Adopted Name for hypromellose (see Martindale, The Extra Pharmacopoeia, 29th edition, page 1435). In the four digit number "2910", the first two digits represent the approximate percentage of methoxyl groups and the third and fourth digits the approximate percentage composition of hydroxypropoxyl groups; 15 mPa·s or 5 mPa·s is a value indicative of the apparent viscosity of a 2% aqueous solution at 20° C.

In the compositions of the invention the organic polymer may conveniently be present up to about 10% by weight, preferably from about 0.1 to about 5%, more preferably from about 0.5 to about 3% by weight (relative to the total weight of the composition).

In case of a solid oral pharmaceutical composition according to the present invention, such as a tablet or a capsule, the composition may also further contain a diluent and/or a glidant.

Pharmaceutical acceptable diluents comprise calcium carbonate, dibasic calcium phosphate, dibasic calcium phosphate dihydrate, tribasic calcium phosphate, calcium sulfate, microstalline cellulose including silicified microcrystalline cellulose, powdered cellulose, dextrates, dextrin, dextrose excipient, fructose, kaolin, lactitol, lactose anhydrous, lactose monohydrate, mannitol, sorbitol, starch, pregelatinized starch, sodium chloride, sucrose, compressible sugar, confectioner's sugar, a spray-dried mixture of lactose monohydrate and microcrystalline cellulose (75:25), commercially available as Microcelac®, a co-processed spray-dried mixture of microcrystalline cellulose and colloidal silicon dioxide (98:2), commercially available as Prosolv®. Preferred is lactose monohydrate, microcrystalline cellulose or silicified microcrystalline cellulose.

Pharmaceutically acceptable glidants comprise talc, colloidal silicon dioxide, starch. magnesium stearate. Preferred is colloidal silicon dioxide.

In case of a tablet, the composition may also further comprise a disintegrant and a lubricant.

Pharmaceutically acceptable disintegrants comprise starch, ion exchange resins, e.g. Amberlite, cross-linked polyvinylpyrrolidone, modified cellulose gum, e.g. croscarmellose sodium (e.g. Ac-di-Sol®), sodium starch glycollate, sodium carboxymethylcellulose, sodium dodecyl sulphate, modified corn starch, microcrystalline cellulose, magnesium aluminium silicate, alginic acid, alginate, powdered cellulose.

Pharmaceutically acceptable lubricants comprise magnesium stearate, calcium stearate, stearic acid, talc, polyethylene glycol, sodium lauryl sulfate, magnesium lauryl sulphate.

Tablets of the present invention may in addition include other optional excipients such as, for example, flavors, sweeteners and colors.

Solid pharmaceutical compositions according to the present invention may comprise by weight based on the total weight of the composition:
(a) from 5 to 50% of a compound of formula (I), (I-a) or (I-b);
(b) from 0.01 to 5% of a wetting agent;
(c) from 40 to 92% of a diluent;
(d) from 0.1 to 5% of a glidant.

Tablets according to the present invention may comprise by weight based on the total weight of the tablet core:
(a) from 5 to 50% of a compound of formula (I), (I-a) or (I-b);
(b) from 0.01 to 5% of a wetting agent;
(c) from 40 to 92% of a diluent;
(d) from 0 to 10% of a polymer;
(e) from 2 to 10% of a disintegrant;
(f) from 0.1 to 5% of a glidant;
(g) from 0.1 to 1.5% of a lubricant.

Tablets of the present invention may optionally be film-coated following art-known coating procedures. Film-coated tablets are easier to swallow than uncoated tablet cores, are usually easier to distinguish from other tablets—in particular when the film-coat contains a dye or a pigment—, may have reduced tackiness, and may furthermore have an improved stability (increased shelf-life), e.g. because the coating may protect the active ingredient from the influence of light. Preferably, the film coat is an immediate release coat. Film coatings may comprise a film-forming polymer and optionally a plasticizer or a pigment. An example of a suitable film-forming polymer is hydroxypropyl methylcellulose, and an example of a suitable plasticizer is polyethyleneglycol, e.g. macrogol 3000 or 6000, or triacetin. Commercially available suitable coatings for pharmaceutical tablets are well-known to a person skilled in the art. Preferably, the film coating is a non-transparant film coating. An example of a suitable coating is Opadry®, in particular coating powder Opadry® II White.

Tablets of the present invention can be prepared by direct compression or wet granulation.

Therefore, the present invention is also concerned with a process of preparing a tablet comprising a compound of formula (I), (I-a) or (I-b) comprising the steps of:

(i) dry blending the active ingredient, the disintegrant and the optional glidant with the diluent;
(ii) optionally mixing the lubricant with the mixture obtained in step (i);
(iii) compressing the mixture obtained in step (i) or in step (ii) in the dry state into a tablet; and
(iv) optionally film-coating the tablet obtained in step (iii).

The present invention is also concerned with a process of preparing a tablet comprising a compound of formula (I), (I-a) or (I-b) comprising the steps of:
(i) dry blending the active ingredient and part of the diluent;
(ii) preparing a binder solution by dissolving the binder and the wetting agent in the binder solution solvent;
(iii) spraying the binder solution obtained in step (ii) on the mixture obtained in step (i);
(iv) drying the wet powder obtained in step (iii) followed by sieving and optionally mixing;
(v) mixing the remaining part of the diluent, the disintegrant and the optional glidant in the mixture obtained in step (iv);
(vi) optionally adding the lubricant to the mixture obtained in step (v);
(vii) compressing the mixture obtained in step (vi) into a tablet;
(viii) optionally film-coating the tablet obtained in step (vii).

A person skilled in the art will recognize the most appropriate equipment to be used for the above-described processes.

The above general route of preparing tablets of the present invention may be modified by a person skilled in the art by for instance adding certain ingredients at other stages than indicated above.

The present compound of formula (I), (I-a) or (I-b) can be used alone or in combination with other therapeutic agents, such as anti-virals, antibiotics, immunomodulators or vaccines for the treatment of viral infections. They may also be used alone or in combination with other prophylactic agents for the prevention of viral infections. The present compounds may be used in vaccines and methods for protecting individuals against viral infections over an extended period of time. The compounds may be employed in such vaccines either alone or together with other anti-viral agents in a manner consistent with the conventional utilization of reverse transcriptase inhibitors in vaccines. Thus, the present compounds may be combined with pharmaceutically acceptable adjuvants conventionally employed in vaccines and administered in prophylactically effective amounts to protect individuals over an extended period of time against HIV infection.

Also, the combination of an antiretroviral compound and a compound of formula (I), (I-a) or (I-b) can be used as a medicine. Thus, the present invention also relates to a product containing (a) a compound of formula (I), (I-a) or (I-b), and (b) one or more other antiretroviral compounds, as a combined preparation for simultaneous, separate or sequential use in anti-HIV treatment. The different drugs may be combined in a single preparation together with pharmaceutically acceptable carriers. Thus, the present invention also relates to a pharmaceutical composition comprising a pharmaceutically acceptable carrier and (a) a therapeutically effective amount of a compound of formula (I), (I-a) or (I-b) and (b) one or more other antiretroviral agents. In particular, the invention also relates to a product containing (a) a compound of formula (I), (I-a) or (I-b), and (b) one or more other antiretroviral compounds, as a combined preparation for simultaneous, separate or sequential use in anti-HIV treatment. More in particular, the invention also relates to a product containing (a) a compound of formula (I), (I-a) or (I-b), and (b) one or more other antiretroviral compounds, as a combined preparation for simultaneous, separate or sequential use in anti-HIV treatment. The different drugs may be combined in a single preparation together with pharmaceutically acceptable carriers. Thus, the present invention also relates to a pharmaceutical composition comprising a pharmaceutically acceptable carrier and (a) a therapeutically effective amount of a compound of formula (I), (I-a) or (I-b) and (b) one or more other antiretroviral agents. In particular, the present invention relates to a pharmaceutical composition comprising a pharmaceutically acceptable carrier and (a) a therapeutically effective amount of a compound of formula (I), (I-a) or (I-b) and (b) one or more other antiretroviral agents. The invention also relates to a pharmaceutical composition comprising a pharmaceutically acceptable carrier and (a) a therapeutically effective amount of a compound of formula (I), (I-a) or (I-b) and (b) one or more other antiretroviral agents.

Said other antiretroviral compounds may be known antiretroviral compounds such as suramine, pentamidine, thymopentin, castanospermine, dextran (dextran sulfate), foscarnet-sodium (trisodium phosphono formate); nucleoside reverse transcriptase inhibitors, e.g. zidovudine (3'-azido-3'-deoxythymidine, AZT), didanosine (2',3'-dideoxyinosine; ddI), zalcitabine (dideoxycytidine, ddC) or lamivudine (2'-3'-dideoxy-3'-thiacytidine, 3TC), stavudine (2',3'-didehydro-3'-deoxythymidine, d4T), abacavir, abacavir sulfate, emtricitabine ((−) FTC), racemic FTC and the like; non-nucleoside reverse transcriptase inhibitors such as nevirapine (11-cyclopropyl-5,11-dihydro-4-methyl-6H-dipyrido-[3,2-b:2',3'-e][1,4]diazepin-6-one), efavirenz, delavirdine, TMC-120, TMC-125 and the like; compounds of the TIBO (tetrahydroimidazo[4,5,1-jk][1,4]-benzodiazepine-2(1H)-one and thione)-type e.g. (S)-8-chloro-4,5,6,7-tetrahydro-5-methyl-6-(3-methyl-2-butenyl)imidazo[4,5,1-jk][1,4]benzodiazepine-2(1H)-thione; compounds of the α-APA (α-anilino phenyl acetamide) type e.g. α-[(2-nitrophenyl)amino]-2,6-dichlorobenzene-acetamide and the like; inhibitors of trans-activating proteins, such as TAT-inhibitors, e.g. RO-5-3335, or REV inhibitors, and the like; protease inhibitors e.g. indinavir, ritonavir, saquinavir, lopinavir (ABT-378), nelfinavir, amprenavir, TMC-114, BMS-232632, VX-175 and the like; fusion inhibitors, e.g. T-20, T-1249 and the like; CXCR4 receptor antagonists, e.g. AMD-3100 and the like; inhibitors of the viral integrase; nucleotide-like reverse transcriptase inhibitors, e.g. tenofovir, tenofovir diphosphate, tenofovir disoproxil fumarate and the like; ribonucleotide reductase inhibitors, e.g. hydroxyurea and the like; CCR5 antagonists, e.g. ancriviroc, aplaviroc hydrochloride, vicriviroc.

By administering the compounds of the present invention with other anti-viral agents which target different events in the viral life cycle, the therapeutic effect of these compounds can be potentiated. Combination therapies as described above exert a synergistic effect in inhibiting HIV replication because each component of the combination acts on a different site of HIV replication. The use of such combinations may reduce the dosage of a given conventional anti-retroviral agent which would be required for a desired therapeutic or prophylactic effect as compared to when that agent is administered as a monotherapy. These combinations may reduce or eliminate the side effects of conventional single anti-retroviral therapy while not interfering with the anti-viral activity of the agents. These combinations reduce potential of resistance to single agent therapies, while minimizing any associated toxicity. These combinations may also increase the efficacy of the conventional agent without increasing the associated toxicity.

The compounds of the present invention may also be administered in combination with immunomodulating agents, e.g. levamisole, bropirimine, anti-human alpha interferon antibody, interferon alpha, interleukin 2, methionine enkephalin, diethyldithiocarbamate, tumor necrosis factor, naltrexone and the like; antibiotics, e.g. pentamidine isethiorate and the like; cholinergic agents, e.g. tacrine, rivastigmine, donepezil, galantamine and the like; NMDA channel blockers, e.g. memantine to prevent or combat infection and diseases or symptoms of diseases associated with HIV infections, such as AIDS and ARC, e.g. dementia.

Although the present invention focuses on the use of the present compounds for preventing or treating HIV infections, the present compounds may also be used as inhibitory agents for other viruses which depend on similar reverse transcriptases for obligatory events in their life cycle.

Experimental Part

A. Synthesis of the Compound of Formula (I-a)

a) 10.99 kg of (E) 4-[[4-[[4-(2-cyanoethenyl)-2,6-dimethylphenyl]amino]-2-pyrimidinyl]amino]benzonitrile and 57 liter acetic acid (2 L/mole) were heated up to 90° C. in a production vessel. The solution was filtered at 95° C. and washed with 3 L acetic acid (0.21 L/mol). 2.973 liter hydrochloric acid (1.1 mole/mole) was added at 80° C. At 85° C. 60 liter water (2 L/mole) was added slowly. The mixture was cooled slowly to 25° C., washed two times with 5.4 liter water and dried at 50° C. The obtained product was milled. Yield: compound of formula (I-a) Form A.

b) About 150 mg of a compound of formula (E) 4-[[4-[[4-(2-cyanoethenyl)-2,6-dimethylphenyl]amino]-2-pyrimidinyl]amino]benzonitrile.HCl and 500 ml propanone were heated in a beaker up to reflux. The obtained fraction was allowed to crystallize at room temperature. The solvent was evaporated under an air flow until a dry product was obtained. Yield: compound of formula (I-a) Form B c) 73.29 kg of (E) 4-[[4-[[4-(2-cyanoethenyl)-2,6-dimethylphenyl]amino]-2-pyrimidinyl]amino]benzonitrile and 300 liter acetic acid (2 L/mole) were heated up to 104° C. in a production vessel. The solution was filtered at 100° C. 19.8 liter hydrochloric acid (1.1 mole/mole) was added at 91.4° C. At 70° C., 150 liter water (2 L/mole) was added slowly. The mixture was cooled slowly to 20° C., washed two times with 75 liter water and dried at 75° C. The obtained product was milled. Yield: compound of formula (I-a) Form C.

d) 10.99 kg of (E) 4-[[4-[[4-(2-cyanoethenyl)-2,6-dimethylphenyl]amino]-2-pyrimidinyl]amino]benzonitrile and 57 liter acetic acid (2 L/mole) were heated up to 93° C. in a production vessel. The solution was filtered at 100° C. and washed with 3 L acetic acid (0.21 L/mol). 2.973 liter hydrochloric acid (1.1 mole/mole) was added at 85° C. 60 liter water (2 L/mole) was added slowly between 85° C.-65° C. The mixture was cooled slowly to 19.5° C., washed two times with 5.4 liter water and dried at 50° C. The obtained product was milled. 230 mg of the product was mixed with 1 ml water and slurried for 1 day at room temperature. Yield: compound of formula (I-a) Form D.

B. Characterization of the Compound of Formula (I-a)

The results of the characterization of Form A, B, C and D by infrared spectroscopy and X-ray powder diffraction (XRPD) analysis are listed below. Results of differential scanning calorimetry (DSC) for Form A are also listed.

Infrared Spectrometry: KBr Dispersion

The compound to be analyzed was mixed with alkali halide and pressed to a pellet (Ph. Eur.).

| apparatus: | Nicolet Magna 560 FTIR spectrophotometer |
|---|---|
| number of scans: | 32 |
| resolution: | 1 cm$^{-1}$ |
| wavelength range: | 4000 to 400 cm$^{-1}$ |
| baseline correction: | yes |
| detector: | DTGS with KBr windows |
| beamsplitter: | Ge on KBr |
| alkali halide: | KBr (potassium bromide) |

Powder XRD

X-ray powder diffraction (XRPD) analyses were carried out on a Philips X'PertPRO MPD diffractometer PW3050/60 with generator PW3040. The instrument is equipped with a Cu LFF X-ray tube PW3373/00.

The compound to be analyzed was spread on a zero background sample holder.

| INSTRUMENT PARAMETERS | |
|---|---|
| generator voltage: | 45 kV |
| generator amperage: | 40 mA |
| geometry: | Bragg-Brentano |
| stage: | spinner stage |
| MEASUREMENT CONDITIONS | |
| scan mode: | continuous |
| scan range: | 3 to 50° 2θ |
| step size: | 0.01675°/step |
| counting time: | 29.845 sec/step |
| spinner revolution time: | 1 sec |
| radiation type: | CuKα |
| radiation wavelength: | 1.54056 Å |

| Incident beam path | | Diffracted beam path | |
|---|---|---|---|
| program. divergence slit: | 15 mm | long anti scatter shield: | + |
| Soller slit: | 0.04 rad | Soller slit: | 0.04 rad |
| beam mask: | 15 mm | Ni filter: | + |
| anti scatter slit: | 1° | detector: | X'Celerator |
| beam knife: | + | | |

Differential Scanning Calorimetry

About 3 mg of the compound to be analyzed was transferred into a standard aluminum TA-Instrument sample pan. The sample pan was closed with the appropriate cover and the DSC curve was recorded on a TA-Instruments Q1000 MTDSC equipped with a RCS cooling unit. The following parameters were used:

| initial temperature: | 20° C. |
|---|---|
| heating rate: | 10° C./min |
| final temperature: | 350° C. |
| nitrogen flow: | 50 ml/min |

Results

Form A-IR

Form A is characterized by an FTIR spectrum with typical absorption bands at about 2217, 1652, 1497, 1435, 1338, 1199 and 550 cm$^{-1}$.

Additional absorption bands are observed at 1631, 1596, 1537, 1504, 1249, 1214, 1179, 1152 and 1070 cm$^{-1}$. (See FIG. 1).

Form A-XRPD

Form A is characterized by typical diffraction peaks at two-theta positions 9.7°±0.2°, 13.5°±0.2° and 15.0°±0.2°. Form A is further characterized by X-ray powder diffraction peaks at two-theta positions 9.1°±0.2°, 11.0°±0.2°, 14.6°±0.2°, 22.0°±0.2°, 25.0°±0.20°, 25.3°±0.2° and 26.7°±0.2°. (See FIG. 2) (Intensity variations can occur due to processes which influence intensities most importantly the processing history of the sample)

Form A-DSC

Form A melts with decomposition. Melting with decomposition starts at about 250° C. and has an onset at about 286° C.

Form B

Form B can be present in two states, a dry state and a wetted state. Only the characteristics of form B in the dry state are given.

Form B-IR

Form B is characterized by an FTIR spectrum with typical absorption bands at about 2227, 2220, 1599, 1500, 1440, 1341, 1209, 549 and 544 cm$^{-1}$.

Additional absorption bands are observed at about 1656, 1538, 1518, 1270, 1179, 1152 and 1070 cm$^{-1}$. (See FIG. 3).

Form B-XRPD

Form B is characterized by typical diffraction peaks at two-theta positions 4.5°±0.2°, 8.8°±0.2°, and 12.5°±0.2°. Form B is further characterized by X-ray powder diffraction peaks at two-theta positions 10.3°±0.2°, 14.7°±0.2°, 20.6°±0.2°, 22.2°±0.2°, and 26.1°±0.2°. (See FIG. 4). (Intensity variations can occur due to processes which influence intensities most importantly the processing history of the sample.)

Form C-IR

Form C is characterized by an FTIR spectrum with typical absorption bands at about 2221, 1654, 1502, 1239, 1193 and 546 cm$^{-1}$.

Additional absorption bands are observed at about. 1627, 1580, 1537, 1492, 1216, 1173, 1157 and 1084 cm$^{-1}$. (See FIG. 5).

Form C-XRPD

Form C is characterized by typical diffraction peaks at two-theta positions 11.9°±0.2°, 14.3°±0.2° and 22.3°±0.2°. Form C is further characterized by X-ray powder diffraction peaks at two-theta positions 12.8°±0.2°, 18.50°±0.2°, 21.2°±0.2°, 24.3°±0.2°, and 26.0°±0.2°. (See FIG. 6) (Intensity variations can occur due to processes which influence intensities most importantly the processing history of the sample.)

Form D-IR

Form D is characterized by an FTIR spectrum with typical absorption bands at about 2218, 1657, 1506, 1448, 1357, 1220 and 547 cm$^{-1}$.

Additional absorption bands are observed at about. 1620, 1597, 1565, 1247, 1214, 1179 1152 and 1073 cm$^{-1}$. (See FIG. 7).

Form D-XRPD

Form D is characterized by typical diffraction peaks at two-theta positions 6.6°±0.2°, 11.6°±0.2°, and 17.1°±0.2°. Form D is further characterized by X-ray powder diffraction peaks at two-theta positions 15.0°±0.2°, 19.2°±0.2°, 20.5°±0.2°, 21.6°±0.2°, and 29.8°±0.2°. (See FIG. 8). (Intensity variations can occur due to processes which influence intensities most importantly the processing history of the sample.)

C. Solubility Data

Table 1 lists solubility data of free base (E) 4-[[4-[[4-(2-cyanoethenyl)-2,6-dimethylphenyl]amino]-2-pyrimidinyl]amino]benzonitrile and of the compound of formula (I-a).

TABLE 1

| Compound | Concentration in mg/ml | | |
| --- | --- | --- | --- |
| | Water | 0.01 N HCl | PEG 400 |
| Free base (E isomer) | 0.00002 | 0.019 | 40 |
| Compound of formula (I-a) (Form A) | 0.0012 | 0.043 | |

The free base as well as the HCl salt have a poor solubility in water as well as in 0.01 N HCl. Free base and HCl salt may be classified as BCS class 2 compounds.

The solubility of the free base is significantly increased in PEG 400.

D. Stability Data a) Chemical Stability

Compound of formula (I-a) (Form A) was stored under different conditions of humidity and temperature.

After storage, the salt was analyzed by High Performance Liquid Chromatography (HPLC) for percentage of impurities.

The results are gathered in Table 2 below. It can be concluded that the compound is chemically stable.

TABLE 2

| Storage condition | Sum of impurities % (%, w/w) | | |
| --- | --- | --- | --- |
| | 1 week | 4 weeks | 8 weeks |
| Reference | 0.43 | — | — |
| 40° C./75% RH | — | 0.42 | 0.44 |
| 50° C./air | — | 0.41 | 0.41 |
| RT/<5% RH | — | 044 | 0.43 |
| RT/56% RH | — | 0.44 | 0.41 |
| RT/75% RH | — | 0.43 | 0.41 |

Explanatory note:
— = not tested
RT = room temperature
RH = Relative Humidity

The compound was also found to be not hygroscopic.

b) Physical stability

The stability of the crystal structure of the compound of formula (I-a) (Form A) was studied after storage for a period of six weeks under different conditions of humidity and temperature. The same conditions as described in Table 2 were applied.

After storage the compound was analyzed with infrared spectroscopy.

No changes in crystal structure were observed, indicating that the compound is crystallographically stable.

The stability of compound of formula (I-a) (Form A) was also studied after storage for 1 year at 5° C. and at 25° C./80% RH. The compound was found to be physically stable.

E. Tablet Formulations

Tablet compositions illustrating the present invention are:

Composition 1a

Tablet core:

| | |
|---|---|
| Compound of formula (I-a) | 27.5 mg (i.e. 25 mg base equivalent) |
| Lactose monohydrate | 242.0 mg |
| Hypromellose 2910 15 mPa · s | 5.6 mg |
| Polysorbate 20 | 1.4 mg |
| Microcrystalline cellulose | 52.5 mg |
| Croscarmellose sodium | 17.5 mg |
| Colloidal silicon dioxide | 1.05 mg |
| Magnesium stearate | 2.45 mg |

Tablet film coat

| | |
|---|---|
| Coating powder Opadry ® II White | 14 mg |
| Purified water* | 80 µl |

Composition 1b

Tablet core:

| | |
|---|---|
| Compound of formula (I-a) | 27.5 mg (i.e. 25 mg base equivalent) |
| Lactose monohydrate | 52.25 mg |
| Hypromellose 2910 5 mPa · s | 1.40 mg |
| Polysorbate 20 | 0.35 mg |
| Microcrystalline cellulose | 13.125 mg |
| Croscarmellose sodium | 4.375 mg |
| Magnesium stearate | 1.00 mg |

Tablet film coat

| | |
|---|---|
| Coating powder Opadry ® II White | 4 mg |
| Purified water* | q.s. |

Composition 1c

Tablet core:

| | |
|---|---|
| Compound of formula (I-a) | 27.5 mg (i.e. 25 mg base equivalent) |
| Lactose monohydrate | 56.97 mg |
| Hypromellose 2910 5 mPa · s | 1.75 mg |
| Polysorbate 20 | 0.35 mg |
| Silicified microcrystalline cellulose | 16.83 mg |
| Croscarmellose sodium | 5.5 mg |
| Magnesium stearate | 1.10 mg |

Tablet film coat

| | |
|---|---|
| Coating powder Opadry ® II White | 4.4 mg |
| Purified water* | q.s. |

Composition 1d

Tablet core:

| | |
|---|---|
| Compound of formula (I-a) | 27.5 mg (i.e. 25 mg base equivalent) |
| Lactose monohydrate | 55.145 mg |
| Polyvinylpyrrolidone | 3.25 mg |
| Polysorbate 20 | 0.35 mg |
| Silicified microcrystalline cellulose | 16.605 mg |
| Croscarmellose sodium | 6.05 mg |
| Magnesium stearate | 1.10 mg |

Tablet film coat

| | |
|---|---|
| Coating powder Opadry ® II White | 4.4 mg |
| Purified water* | q.s. |

Composition 2a

Tablet core:

| | |
|---|---|
| Compound of formula (I-a) | 110 mg (i.e. 100 mg base equivalent) |
| Lactose monohydrate | 159.5 mg |
| Hypromellose 2910 15 mPa · s | 5.6 mg |
| Polysorbate 20 | 1.4 mg |
| Microcrystalline cellulose | 52.5 mg |
| Croscarmellose sodium | 17.5 mg |
| Colloidal silicon dioxide | 1.05 mg |
| Magnesium stearate | 2.45 mg |

Tablet film coat

| | |
|---|---|
| Coating powder Opadry ® II White | 14 mg |
| Purified water* | 80 µl |

Composition 2b

Tablet core:

| | |
|---|---|
| Compound of formula (I-a) | 110 mg (i.e. 100 mg base equivalent) |
| Lactose monohydrate | 209.00 mg |
| Hypromellose 2910 5 mPa · s | 5.6 mg |
| Polysorbate 20 | 1.4 mg |
| Microcrystalline cellulose | 52.5 mg |
| Croscarmellose sodium | 17.5 mg |
| Magnesium stearate | 4.00 mg |

Tablet film coat

| | |
|---|---|
| Coating powder Opadry ® II White | 16 mg |
| Purified water* | q.s. |

Composition 2c

Tablet core:

| | |
|---|---|
| Compound of formula (I-a) | 110 mg (i.e. 100 mg base equivalent) |
| Lactose monohydrate | 227.88 mg |
| Hypromellose 2910 5 mPa · s | 7.00 mg |
| Polysorbate 20 | 1.4 mg |
| Silicified microcrystalline cellulose | 67.32 mg |
| Croscarmellose sodium | 22.00 mg |
| Magnesium stearate | 4.40 mg |

Tablet film coat

| | |
|---|---|
| Coating powder Opadry ® II White | 17.6 mg |
| Purified water* | q.s. |

Composition 2d

Tablet core:

| | |
|---|---|
| Compound of formula (I-a) | 110 mg (i.e. 100 mg base equivalent) |
| Lactose monohydrate | 220.58 mg |
| Polyvinylpyrrolidone | 13.00 mg |
| Polysorbate 20 | 1.4 mg |
| Silicified microcrystalline cellulose | 66.42 mg |
| Croscarmellose sodium | 24.2 mg |
| Magnesium stearate | 4.40 mg |

Tablet film coat

| | |
|---|---|
| Coating powder Opadry ® II White | 17.6 mg |
| Purified water* | q.s. |

Composition 3a

Tablet core:

| | |
|---|---|
| Compound of formula (I-a) | 55 mg (i.e. 50 mg base equivalent) |
| Lactose monohydrate | 214.5 mg |
| Hypromellose 2910 15 mPa · s | 5.6 mg |
| Polysorbate 20 | 1.4 mg |
| Microcrystalline cellulose | 52.5 mg |
| Croscarmellose sodium | 17.5 mg |
| Colloidal silicon dioxide | 1.05 mg |
| Magnesium stearate | 2.45 mg |

Tablet film coat

| | |
|---|---|
| Coating powder Opadry ® II White | 14 mg |
| Purified water* | 80 µl |

Composition 3b

Tablet core:

| | |
|---|---|
| Compound of formula (I-a) | 55 mg (i.e. 50 mg base equivalent) |
| Lactose monohydrate | 104.50 mg |
| Hypromellose 2910 5 mPa · s | 2.80 mg |

-continued

| | |
|---|---|
| Polysorbate 20 | 0.70 mg |
| Microcrystalline cellulose | 26.25 mg |
| Croscarmellose sodium | 8.75 mg |
| Magnesium stearate | 2.00 mg |
| Tablet film coat | |
| Coating powder Opadry ® II White | 8.00 mg |
| Purified water* | q.s. |

Composition 3c

Tablet core:

| | |
|---|---|
| Compound of formula (I-a) | 55 mg (i.e. 50 mg base equivalent) |
| Lactose monohydrate | 113.94 mg |
| Hypromellose 2910 5 mPa · s | 3.50 mg |
| Polysorbate 20 | 0.70 mg |
| Silicified microcrystalline cellulose | 33.66 mg |
| Croscarmellose sodium | 11.0 mg |
| Magnesium stearate | 2.20 mg |
| Tablet film coat | |
| Coating powder Opadry ® II White | 8.80 mg |
| Purified water* | q.s. |

Composition 3d

Tablet core:

| | |
|---|---|
| Compound of formula (I-a) | 55 mg (i.e. 50 mg base equivalent) |
| Lactose monohydrate | 110.29 mg |
| Polyvinylpyrrolidone | 6.50 mg |
| Polysorbate 20 | 0.70 mg |
| Silicified microcrystalline cellulose | 33.21 mg |
| Croscarmellose sodium | 12.1 mg |
| Magnesium stearate | 2.20 mg |
| Tablet film coat | |
| Coating powder Opadry ® II White | 8.80 mg |
| Purified water* | q.s. |

Composition 4

Tablet core:

| | |
|---|---|
| Compound of formula (I-a) | 82.5 mg (i.e. 75 mg base equivalent) |
| Lactose monohydrate | 165.435 mg |
| Polyvinylpyrrolidone | 9.75 mg |
| Polysorbate 20 | 1.05 mg |
| Silicified microcrystalline cellulose | 49.815 mg |
| Croscarmellose sodium | 18.15 mg |
| Magnesium stearate | 3.30 mg |
| Tablet film coat | |
| Coating powder Opadry ® II White | 13.2 mg |
| Purified water* | q.s. |

Composition 5a

Tablet core:

| | |
|---|---|
| Compound of formula (I-a) | 165 mg (i.e. 150 mg base equivalent) |
| Lactose monohydrate | 330.87 mg |
| Polyvinylpyrrolidone | 19.5 mg |
| Polysorbate 20 | 2.1 mg |
| Silicified microcrystalline cellulose | 99.63 mg |
| Croscarmellose sodium | 36.30 mg |
| Magnesium stearate | 6.6 mg |
| Tablet film coat | |
| Coating powder Opadry ® II White | 19.80 mg |
| Purified water* | q.s. |

Composition 5b

Tablet core:

| | |
|---|---|
| Compound of formula (I-a) | 165 mg (i.e. 150 mg base equivalent) |
| Lactose monohydrate | 341.82 mg |

-continued

| | |
|---|---|
| Hypromellose 2910 5 mPa · s | 10.5 mg |
| Polysorbate 20 | 2.1 mg |
| Silicified microcrystalline cellulose | 100.98 mg |
| Croscarmellose sodium | 33.00 mg |
| Magnesium stearate | 6.6 mg |
| Tablet film coat | |
| Coating powder Opadry ® II White | 19.80 mg |
| Purified water* | q.s. |

*not present in final tablet

The above tablets were prepared by dissolving hypromellose or polyvinylpyrrolidone and polysorbate 20 in purified water (q.s.) followed by spraying said solution on fluidized powder consisting of a mixture of Form A and lactose monohydrate. The obtained granulate was dried, sieved and mixed with microcrystalline cellulose or silicified microcrystalline cellulose, croscarmellose sodium and optionally colloidal silicon dioxide. After addition of Magnesium stearate, the powder mixture was compressed into tablets followed by film coating the tablets with a suspension of Coating powder Opadry® II White in purified water.

In the above compositions, microcrystalline cellulose is preferably Avicel® PH101, croscarmellose sodium is preferably Ac-Di-Sol®; silicified microcrystalline cellulose is preferably Prosolv® HD90; polyvinylpyrrolidone is preferably PVP K29-32.

F. In vivo bioavailability study

A) In order to study the in vivo bioavailability of the compound of formula (I-a), a study in male beagle dogs was performed.

The bioavailability of the compound of formula (I-a) after oral administration was compared with the bioavailability of the free base after intravenous administration. The formulation used for intravenous administration was a 75% PEG 400/25% sterile water solution of (E) 4-[[4-[[4-(2-cyanoethenyl)-2,6-dimethylphenyl]amino]-2-pyrimidinyl]amino] benzonitrile free base administered at a dose of 1.25 mg/kg.

The formulations used for oral administration were:
 a PEG 400 solution of (E) 4-[[4-[[4-(2-cyanoethenyl)-2,6-dimethylphenyl]amino]-2-pyrimidinyl]amino]benzonitrile free base (group I);
 a capsule (size 0; red cap-red body) containing 7.67% (w/w) of 4-[[4-[[4-(2-cyanoethenyl)-2,6-dimethylphenyl]amino]-2-pyrimidinyl]amino]benzonitrile (E) free base, 0.18% (w/w) sodium lauryl sulfate, 0.18% (w/w) silicon dioxide, 91.97% (w/w) granulated lactose monohydrate (group II);
 a capsule (size 0; red cap-red body) containing 8.36% (w/w) of a compound of formula (I-a), 0.18% (w/w) sodium lauryl sulfate, 0.18% (w/w) silicon dioxide, 91.28% (w/w) granulated lactose monohydrate (group III).

(the % w/w is based on the capsule content)

The different formulations were orally administered at a dose level of 5 mg base equivalent/kg. The formulations were prepared based on previously determined body weights of the animals. The exact administered dose was calculated using the body weights just before dosing and amounted on average to 5 mg base equivalent/kg per formulation.

Blood samples (4 ml on EDTA) were taken from a jugular vein from the dogs at 0 (=predose), 0.5, 1, 2, 4, 6, 8, 24, 32, 48 and 72 h after dose administration. After sampling, the blood samples were immediately placed on melting ice and protected from light. Blood samples were centrifuged at approximately 1900×g for 10 minutes at 5° C. to allow plasma separation. Plasma samples were separated, transferred into a second tube within 2 h after blood sampling and stored at ≦−18° C. until analysis. At all times, samples were protected from light and placed on melting ice or at ≦−18° C.

Plasma levels of 4-[[4-[[4-(2-cyanoethenyl)-2,6-dimethylphenyl]amino]-2-pyrimidinyl]amino]benzonitrile (E) were determined using a qualified research LC-MS/MS method. LC-MS/MS analysis was carried out on an API-3000 MS/MS (Applied Biosystems), which was coupled to an HPLC-pump (Agilent) and autosampler (Interscience).

Mean (n=2) plasma concentrations per formulation and per sampling time were calculated. Peak plasma concentrations ($C_{max}$), corresponding peak times ($T_{max}$) and $AUC_{0-t}$ (where t is the time point corresponding to the last measurable concentration above the quantification limit) were determined. The area under the curve extrapolated to infinity ($AUC_{0-inf}$) was calculated as the sum of $AUC_{0-t}$ and Ct/β, where β is the elimination rate constant, determined by log-linear regression of the terminal plasma concentration-time data. Mean (n=2) PK parameters were calculated for all formulations. An estimate of the absolute bioavailability ($F_{abs}$) of 4-[[4-[[4-(2-cyanoethenyl)-2,6-dimethylphenyl]amino]-2-pyrimidinyl]amino]benzonitrile (E) was obtained by dividing dose-normalised mean $AUC_{0-inf}$ value after oral administration by dose-normalised mean $AUC_{0-inf}$ value after intravenous administration and this for all oral formulations.

The results gathered in the above described study are summarized in Table 3.

TABLE 3

| | Formulation | | | |
|---|---|---|---|---|
| | IV | Oral group I | Oral group II | Oral group III |
| | | | Dose | |
| Time (hour) | 1.25 mg/kg Mean conc. (ng/ml) (n = 2) | 5 mg/kg Mean Conc. (ng/ml) (n = 2) | 5 mg/kg Mean Conc. (ng/ml) (n = 2) | 5 mg/kg Mean Conc. (ng/ml) (n = 2) |
| 0 | | | | |
| 0.13 | 644 | | | |
| 0.25 | 696 | | | |
| 0.5 | 582 | 102 | <1.00 | 57.2 |
| 1 | 482 | 206 | 5.19 | 367 |
| 2 | 426 | 277 | 18.9 | 542 |
| 4 | 315 | 288 | 21.2 | 407 |
| 6 | 241 | 265 | 16.2 | 387 |
| 8 | 129 | 257 | 13.4 | 333 |
| 24 | 114 | 131 | 6.68 | 126 |
| 32 | 70.3 | 92.7 | 5.75 | 136 |
| 48 | 55.5 | 63.3 | 2.87 | 66.1 |
| 72 | 29.5 | 44.7 | <1.00 | 36.6 |
| $C_{max}$ ng/ml | | 341 | 21 | 542 |
| $T_{max}$ h | | 4 | 4 | 2 |
| $AUC_{0-72 h}$ ng · h/ml | 7330 | 8359 | 308 (n = 1) | 10231 |
| $AUC_{0-INF}$ ng · h/ml | 8661 | 10854 | 464 | 11770 |
| $F_{abs}$ | | 31% | 1.34% | 34.0% |

From the results above it can be concluded that, when administered as a solid dosage form, the compound of formula (I-a) has a significant better bioavailability than the corresponding free base 4-[[4-[[4-(2-cyanoethenyl)-2,6-dimethylphenyl]amino]-2-pyrimidinyl]amino]benzonitrile (E). The bioavailability is comparable with that of the free base administered as an oral PEG 400 solution.

B) The oral bioavailability of the compound of formula (I-a) was also studied in vivo in humans.

The healthy subjects received 2 treatments.

Treatment A: a 25 mg/ml solution of free base (E) 4-[[4-[[4-(2-cyanoethenyl)-2,6-dimethylphenyl]amino]-2-pyrimidinyl]amino]benzonitrile in 100% PEG 400.

Treatment B: a tablet according to composition 2a described hereinabove.

In a panel of 12 subjects, each subject received three single doses, each equivalent to 100 mg of the free base (E) 4-[[4-[[4-(2-cyanoethenyl)-2,6-dimethylphenyl]amino]-2-pyrimidinyl]amino]benzonitrile. Each dose was administered on day 1 of the respective treatment period.

The subjects (n=12) were randomized to receive single doses of Treatment A under fed conditions, Treatment B in the fasted state and Treatment B under fed conditions during three sessions, each separated by a wash-out period of at least 2 weeks. A 216-hour pharmacokinetic profile for (E) 4-[[4-[[4-(2-cyanoethenyl)-2,6-dimethylphenyl]amino]-2-pyrimidinyl]amino]benzonitrile in plasma was determined for each session after oral administration of a single 100 mg dose of (E)-4-[[4-[[4-(2-cyanoethenyl)-2,6-dimethylphenyl]amino]-2-pyrimidinyl]amino]benzonitrile base or equivalent. For the determination of plasma (E)-4-[[4-[[4-(2-cyanoethenyl)-2,6-dimethylphenyl]amino]-2-pyrimidinyl]amino]benzonitrile concentrations, blood was drawn predose, and at 0.5, 1, 2, 3, 4, 6, 8, 12, 16, 24, 32, 48, 72, 96, 120, 144, 168 and 216 hours after administration of the study medication (19 samples in total per subject per administration).

For each subject, two of the three doses were administered under fed conditions, i.e. a standardized breakfast was consumed within 10 minutes prior to dosing with Treatment A or Treatment B, when the pharmacokinetics were investigated under fed conditions. For 'fasted' conditions, subjects had to be fasted for at least 10 hours before administration of the investigational drug. They received their first meal at lunch, 4.5 hours after administration of the investigational drug, when the pharmacokinetics were investigated under fasted conditions (Treatment B only).

In particular, on day −1, subjects were admitted to the testing facility and fasted overnight for at least 10 hours, except for the intake of water which was allowed until 2 hours before drug intake. For subjects randomized to receive Treatment A or Treatment B under fed conditions, the trial medication was administered within 10 minutes after a standardized breakfast in the testing facility. For subjects randomized to receive Treatment B in the fasted state, the trial medication was taken without food, after an overnight fast of at least 10 hours.

The standardized breakfast consisted of four slices of bread, two slices of ham or cheese, butter, jam and two cups of decaffeinated coffee or tea with milk and/or sugar. This meal was ingested within 20 minutes under the supervision of a trial nurse or staff member.

For all subjects, trial medication was administered together with approximately 200 mL of water between 9 a.m. and 11 a.m.

From 2 hours after dosing, intake of water was allowed for all subjects. Lunch was served 4.5 hours after dosing and dinner was served 10 hours after dosing. After dinner, subjects were allowed to resume their usual diet.

The subjects were discharged from the testing facility on Day 2 after the 24 hour post-dose pharmacokinetic sample and returned to the facility 8 hours later and again on Days 3, 4, 5, 6, 7, 8 and 10 for further assessments. In more detail: for the determination of plasma (E)-4-[[4-[[4-(2-cyanoethenyl)-2,6-dimethylphenyl]amino]-2-pyrimidinyl]amino]benzonitrile concentrations, blood was drawn predose, and at 0.5, 1, 2, 3, 4, 6, 8, 12, 16, 24, 32, 48, 72, 96, 120, 144, 168 and 216 hours after administration of the study medication (19 samples in total per subject per administration).

For each individual subject, there was a time interval of at least 2 weeks between dose administrations.

The bioanalysis of (E)-4-[[4-[[4-(2-cyanoethenyl)-2,6-dimethylphenyl]amino]-2-pyrimidinyl]amino]benzonitrile in human plasma was performed by a validated LC-MS/MS method.

Table 4 gathers the results of the human in vivo study.

TABLE 4

| Pharmacokinetics of (E)-4-[[4-[[4-(2-cyanoethenyl)-2,6-dimethylphenyl]amino]-2-pyrimidinyl]amino]benzonitrile | Treatment A | Treatment B | |
|---|---|---|---|
| (mean ± SD) | fed | fed | fasted |
| N | 12 | 12 | 12 |
| $C_{max}$ (ng/mL) | 372 (37) | 316 (59) | 210 (119) |
| $AUC_{last}$ (ng·h/mL) | 12448 (2688) | 10455 (2525) | 7421 (2939) |
| $AUC_\infty$ (ng·h/mL) | 12945 (2988) | 10905 (2754) | 7804 (3101) |

The invention claimed is:

1. A pharmaceutical composition comprising a pharmaceutically acceptable carrier and a compound of formula (I-a)

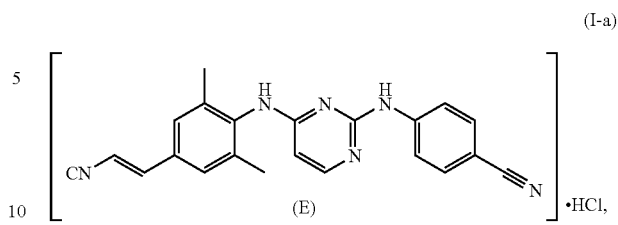

wherein said pharmaceutically acceptable carrier comprises:
from 0.01 to 5% of said pharmaceutical composition of a wetting agent;
from 40 to 92% of said pharmaceutical composition of a diluent;
from 0 to 10% of said pharmaceutical composition of a polymer;
from 2 to 10% of said pharmaceutical composition of a disintegrant;
from 0.1 to 5% of said pharmaceutical composition of a glidant; and
from 0.1 to 1.5% of said pharmaceutical composition of a lubricant;
and wherein said compound of formula (I-a) is present in said pharmaceutical composition at from 5-50% of said pharmaceutical composition.

* * * * *

UNITED STATES PATENT AND TRADEMARK OFFICE
CERTIFICATE OF CORRECTION

| | | |
|---|---|---|
| PATENT NO. | : 7,638,522 B2 | Page 1 of 1 |
| APPLICATION NO. | : 11/219163 | |
| DATED | : December 29, 2009 | |
| INVENTOR(S) | : Guillemont et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 287 days.

Signed and Sealed this
Eleventh Day of January, 2011

David J. Kappos
*Director of the United States Patent and Trademark Office*